US007521528B2

(12) United States Patent
Gardella et al.

(10) Patent No.: US 7,521,528 B2
(45) Date of Patent: Apr. 21, 2009

(54) CONFORMATIONALLY CONSTRAINED PARATHYROID HORMONE (PTH) ANALOGS WITH LACTAM BRIDGES

(75) Inventors: Thomas J. Gardella, Needham, MA (US); Henry M. Kronenberg, Boston, MA (US); John T. Potts, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/542,704

(22) PCT Filed: Jan. 24, 2003

(86) PCT No.: PCT/US03/02155

§ 371 (c)(1),
(2), (4) Date: Apr. 14, 2006

(87) PCT Pub. No.: WO2004/067021

PCT Pub. Date: Aug. 12, 2004

(65) Prior Publication Data

US 2006/0229240 A1    Oct. 12, 2006

(51) Int. Cl.
*C07K 14/635* (2006.01)
(52) U.S. Cl. .................. 530/324; 530/325; 530/326; 530/399; 514/12
(58) Field of Classification Search ................ 530/324, 530/325, 326, 399
See application file for complete search history.

(56) References Cited

U.S. PATENT DOCUMENTS

| 4,675,189 | A | 6/1987 | Kent et al. |
| 4,698,328 | A | 10/1987 | Neer et al. |
| 4,761,406 | A | 8/1988 | Flora et al. |
| 5,880,093 | A | 3/1999 | Bagnoli |
| 6,495,662 | B1 | 12/2002 | Gardella et al. |

FOREIGN PATENT DOCUMENTS

WO    WO 01/23521    4/2001

OTHER PUBLICATIONS

Shimizu, Naoto (Biochemistry 42(8), 2282-2290, 2003).*
Barbier, J.-R. (J. Med. Chem. 40:1373-1380, 1997).*
Barden, J.A. and Kemp, B.E., "NMR Solution Structure of Human Parathyroid Hormone(1-34)," *Biochemistry* 32:7126-7132, American Chemical Society (1993).
Behar, V., et al., "Photoaffinity Cross-linking Indentifies Differences in the Interactions of an Agonist and an Antagonist with the Parathyroid Hormone/Parathyroid Hormone-related Protein Receptor," *J. Biol. Chem.* 275:9-17, American Society for Biochemistry and Molecular Biology, Inc. (2000).
Bergwitz, C., et al., "Full Activation of Chimeric Receptors by Hybrids between Parathyroid Hormone and Calcitonin," *J. Biol. Chem.* 271:26469-26472, The American Society for Biochemistry and Molecular Biology, Inc. (1996).
Berridge, M.J., et al., "Changes in the levels of inositol phosphates after agonist-dependent hydrolysis of membrane phosphoinositides," *Biochem. J.* 212:473-482, The Biochemical Society (1983).
Blackburn, C. and Kates, S.A., "Solid-Phase Synthesis of Cyclic Homodetic Peptides," *Meth. Enzymol.* 289:175-198, Academic Press (1997).
Bowen, W.P. and Jerman, J.C., "Nonlinear regression using spreadsheets," *Trends Pharmacol. Sci.* 16:413-417, Elsevier Science, Ltd. (1995).
Carter, P.H., et al., "Studies of the N-Terminal Region of a Parathyroid Hormone-Related Peptide(1-36) Analog: Receptor Subtype-Selective Agonists, Antagonists, and Photochemical Cross-Linking Agents," *Endocrinol.* 140:4972-4981, The Endocrine Society (1999).
Chen, Z., et al., "Solution Structure of the Osteogenic 1-31 Fragment of the Human Parathyroid Hormone," *Biochemistry* 39:12766-12777, American Chemical Society (2000).
Condon, S.M., et al., "The Bioactive Conformation of Human Parathyroid Hormone. Structural Evidence for the Extended Helix Postulate," *J. Am. Chem. Soc.* 122:3007-3014, American Chemical Society (2000).
Creighton, T.E., ed., "3.2. Evolutionary Divergence of Proteins," in: *Proteins: Structures and Molecular Properties*, 2nd Ed., W.H. Freeman and Co., New York, NY, pp. 108-114 (1993).
Dempster, D.W., et al., "Anabolic Actions of Parathyroid Hormone on Bone," *Endocrine Rev.* 14:690-709, The Endocrine Society (1993).
Dempster, D.W., et al., "Erratum: Anabolic Actions of Parathyroid Hormone on Bone," *Endocrine Rev.* 15:261, The Endocrine Society (1994).
Fairwell, T., et al., "Total Solid-Phase Synthesis, Purification, and Characterization of Human Parathyroid Hormone-(1-84)," *Biochemistry* 22:2691-2697, American Chemical Society (1983).

(Continued)

*Primary Examiner*—David Lukton
(74) *Attorney, Agent, or Firm*—Clark & Elbing LLP

(57) ABSTRACT

The present invention relates to methods of treatment of mammalian conditions characterized by decreases in bone mass with conformationally constrained parathyroid hormone (PTH) analogs and derivatives of those analogs containing PTH polypeptide derivatives containing at least one Glu or Lys substitution at position 6 and/or 10, some with installed lactam bridges between the side chains of Lys and Glu. The invention provides derivatives of PTH (1-34), PTH (1-33), PTH(1-32), PTH(1-31), PTH(1-30), PTH(1-29), PTH (1-28), PTH(1-27), PTH(1-26), PTH(1-25), PTH(1-24), PTH (1-23), PTH(1-22), PTH (1-21), PTH(1-20), PTH(1-19), PTH(1-18), PTH(1-17), PTH(1-16), PTH(1-15), PTH(1-14), PTH(1-13), PTH(1-12), PTH(1-11), PTH(1-10) and PTH(1-9) polypeptide. The invention also provides methods of preparing the PTH analogs. Further, the invention encompasses treating conditions that are characterized by undesired bone loss or by the need for bone growth, e.g. in treating fractures or cartilage disorders and for raising cAMP levels in cells where deemed necessary.

18 Claims, 4 Drawing Sheets

OTHER PUBLICATIONS

Gronwald, W., et al., "Structure of Recombinant Human Parathyroid Hormone in Solution Using Multidimensional NMR Spectroscopy," *Biol. Chem. Hoppe-Seyler* 377:175-186, Walter de Gruyter & Co. (1996).

Goud, N.A., et al., "Solid-Phase Synthesis and Biologic Activity of Human Parathyroid Hormone(1-84)," *J. Bone Min. Res.* 6:781-789, Mary Ann Liebert, Inc. (1991).

Hoare, S.R.J., et al., "Evaluating the Signal Transduction Mechanism of the Parathyroid Hormone 1 Receptor," *J. Biol. Chem.* 276:7741-7753, American Society for Biochemistry and Molecular Biology (2001).

Jüppner, H., et al., "A G Protein-Linked Receptor for Parathyroid Hormone and Parathyroid Hormone-Related Peptide," *Science* 254:1024-1026, American Society for the Advancement of Science (1991).

Kronenberg, H.M., et al., "Parathyroid Hormone: Biosynthesis, Secretion, Chemistry, and Action" in: *Handbook of Experimental Pharmacology*, Mundy, G.R., and Martin, T.J., eds., Springer-Verlag, Berlin, Germany, pp. 507-567 (1993).

Luck, M.D., et al., "The (1-14) Fragment of Parathyroid Hormone (PTH) Activates Intact and Amino-Terminally Truncated PTH-1 Receptors," *Mol. Endocrinol.* 13:670-680, The Endocrine Society (1999).

Marx, U.C., et al., "Structure of Human Parathyroid Hormone 1-37 in Solution," *J. Biol. Chem.* 270:15194-15202, The American Society for Biochemistry and Molecular Biology, Inc. (1995).

Marx, U.C., et al., "Structure Activity Relation of $NH_2$-Terminal Human Parathyroid Hormone Fragments," *J. Biol. Chem* 273:4308-4316, American Society for Biochemistry and Molecular Biology, Inc. (1998).

Marx, U.C., et al., "Solution Structure of Human Parathyroid Hormone Fragments hPTH(1-34) and hPTH (1-39) and Bovine Parathyroid Hormone Fragment bPTH(1-37)," *Biochem. Biophys. Res. Commun.* 267:213-220, Academic Press (2000).

Neer, R.M., et al., "Effect of Parathyroid Hormone (1-34) On Fractures and Bone Mineral Density in Postmenopausal Women with Osteoporosis," *N. Eng. J. Med.* 344:1434-1441, Massachusetts Medical Society (2001).

Pellegrini, M., et al., "Binding Domain of Human Parathyroid Hormone Receptor: From Conformation to Function," *Biochemistry* 37:12737-12743, American Chemical Society (1998).

Robinson J.R. ed., "Methods to Achieve Controlled Drug Delivery," in: *Sustained and Controlled Release Drug Delivery Systems*, Marcel Dekker, New York, NY, pp. 557-593 (1978).

Shen, V., et al., "Effects of Combined and Separate Intermittent Administration of Low-Dose Human Parathyroid Hormone Fragment (1-34) and 17β-Estradiol on Bone Histomorphometry in Ovariectomized Rats with Established Osteopenia," *Calcif. Tissue Int.* 50:214-220, Springer-Verlag Inc. (1992).

Shimizu, M. et al., "Autoactivation of Type-1 Parathyroid Hormone Receptors Containing a Tethered Ligand," *J. Biol. Chem.* 275:19456-19460, The American Society for Biochemistry and Molecular Biology, Inc. (2000).

Shimizu, M., et al., "Minimization of Parathyroid Hormone," *J. Biol. Chem.* 275:21836-21843, The American Society for Biochemistry and Molecular Biology, Inc. (2000).

Shimizu, M., et al., "Enhanced Activity in Parathyroid Hormone-(1-14) and -(1-11): Novel Peptides for Probing Ligand-Receptor Interactions," *Endocrinol.* 142:3068-3073, Endocrine Society (2001).

Shimizu, N., et al., "Parathyroid Hormone (PTH)-(1-14) and -(1-11) Analogs Conformationally Constrained by α-Aminoisobutyric Acid Mediate Full Agonist Responses via the Juxtamembrane Region of the PTH-1 Receptor," *J. Biol. Chem.* 276:49003-49012, The American Society for Biochemistry and Molecular Biology, Inc. (2001).

Slovik, D.M., et al., "Restoration of Spinal Bone in Osteoporotic Men by Treatment with Human Parathyroid Hormone (1-34) and 1,25-Dihydroxyvitamin D," *J. Bone Min. Res.* 1:377-381, Mary Ann Liebert, Inc. (1986).

Takasu, H., et al., "Amino Terminal Modifications of Human Parathyroid Hormone (PTH) Selectively Alter Phospholipase C Signaling via the Type 1 PTH Receptor: Implications for Design for Signal-Specific PTH Ligands," *Biochemistry* 38:13453-13460, American Chemical Society (1999).

Takasu, H., et al., "Dual Signaling and Ligand Selectively of the Human PTH/PTHrP Receptor," *J. Bone Min. Res.* 14:11-20, Blackwell Science, Inc. (1999).

Tregear, G.W., et al., "Bovine Parathyroid Hormone: Minimum Chain Length of Synthetic Peptide Required for Biological Activity," *Endocrinol.* 93:1349-1353, The Endocrine Society (1973).

Whitefield, J.F., et al., "Restoration of Severely Depleted Femoral Trabecular Bone in Ovariectomized Rats by Parathyroid Hormone-(1-34)," *Calcif. Tissue Int.* 56:227-231, Springer-Verlag Inc. (1995).

Whitfield, J.F., et al., "Comparison of the Ability of Recombinant Human Parathyroid Hormone, rhPTH-(1-84), and hPTH-(1-31)$NH_2$ to Stimulate Femoral Trabecular Bone Growth in Ovariectomized Rats," *Calcif. Tissue Int.* 60:26-29, Springer-Verlag Inc. (1997).

Wold, F., "Posttranslational Protein Modifications: Perspectives and Prospects," in *Posttranslational Covalent Modifications of Proteins*, B.C. Johnson, eds., Academic Press, Inc., New York, pp. 1-12 (1983).

\* cited by examiner

CONFORMATIONALLY CONSTRAINED PARATHYROID HORMONE (PTH) ANALOGS WITH LACTAM BRIDGES

STATEMENT REGARDING FEDERALLY-SPONSORED RESEARCH AND DEVELOPMENT

Statement under MPEP 310. The U.S. Government has a paid-up license in this invention and the right in limited circumstances to require the patent owner to license others on reasonable terms as provided for by the terms of Grant No. DK-11794 awarded by the National Institutes of Health.

CROSS-REFERENCE TO RELATED APPLICATIONS

This application is a national phase of International Appl. No. PCT/US2003/002155, filed Jan. 24, 2003, which published under PCT Article 21(2) in English and which is herein incorporated by reference.

BACKGROUND OF THE INVENTION

1. Field of the Invention

The present invention relates to conformationally constrained parathyroid hormone (PTH) analogs, and methods of preparing and using the PTH analogs.

2. Background Art

Parathyroid Hormone

Parathyroid hormone (PTH), an 84 amino acid peptide, is the principal regulator of ionized blood calcium in the human body (Kronenberg, H. M., et al., In *Handbook of experimental Pharmacology*, Mundy, G. R., and Martin, T. J., (eds), pp. 185-201, Springer-Verlag, Heidelberg (1993)). Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH is thought to exert these effects primarily through receptor-mediated activation of adenylate cyclase and/or phospholipase C.

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a parathyroid gland lesion (e.g., adenoma, hyperplasia, or carcinoma). Another type of hypercalcemia, humoral hypercalcemia of malignancy (HHM) is the most common paraneoplastic syndrome. It appears to result in most instances from the production by tumors (e.g., squamous, renal, ovarian, or bladder carcinomas) of a class of protein hormone which shares amino acid homology with PTH. These PTH-related proteins (PTHrP) appear to mimic certain of the renal and skeletal actions of PTH and are believed to interact with the PTH receptor in these tissues.

Osteoporosis

Osteoporosis is a potentially crippling skeletal disease observed in a substantial portion of the senior adult population, in pregnant women and even in juveniles. The term osteoporosis refers to a heterogeneous group of disorders. Clinically, osteoporosis is separated into type I and type II. Type I osteoporosis occurs predominantly in middle aged women and is associated with estrogen loss at menopause, while osteoporosis type II is associated with advancing age. Patients with osteoporosis would benefit from new therapies designed to promote fracture repair, or from therapies designed to prevent or lessen the fractures associated with the disease.

The disease is marked by diminished bone mass, decreased bone mineral density (BMD), decreased bone strength and an increased risk of bone fracture. At present, there is no effective cure for osteoporosis, though estrogen, calcitonin and the bisphosphonates, etidronate and alendronate are used to treat the disease with varying levels of success. These agents act to decrease bone resorption. Since parathyroid hormone regulates blood calcium and the phosphate levels, and has potent anabolic (bone-forming) effects on the skeleton, in animals (Shen, V., et al., *Calcif. Tissue Int.* 50:214-220 (1992); Whitefild, J. F., et al., *Calcif. Tissue Int.* 56:227-231 (1995) and Whitfield, J. F., et al., *Calcif. Tissue Int.* 60:26-29 (1997)) and humans (Slovik, D. M., et al., *J. Bone Miner. Res.* 1:377-381 (1986); Dempster, D. W., et al., *Endocr. Rev.* 14:690-709 (1993) and Dempster, D. W., et al., *Endocr. Rev.* 15:261 (1994)) when administered intermittently, PTH, or PTH derivatives, are prime candidates for new and effective therapies for osteoporosis.

PTH Derivatives

PTH derivatives include polypeptides that have amino acid substitutions or are truncated relative to the full length molecule. A 14, 21, and a 34 amino acid amino-terminal truncated form of PTH, as well as a C-terminal truncated form have been studied. Additionally, amino acid substitutions within the truncated polypeptides have also been investigated.

Synthetic PTH(1-34) exhibits fall bioactivity in most cell-based assay systems, has potent anabolic effects on bone mass in animals and has been shown to reduce the risk of bone fracture in postmenopausal osteoporotic women (Neer, R. M., et al., *N. E. J. M.* 344:1434-1441 (2001); Dempster, D. W., et al., *Endocr Rev* 14:690-709 (1993)). PTH acts on the PTH/PTHrP receptor (P1R), a class II G protein-coupled heptahelical receptor that couples to the adenylyl cyclase/cAMP and phospolipase C/inositol phosphate (IP) signaling pathway (Rippner, H., et al., *Science* 254:1024-1026 (1991)). Deletion analysis studies have shown that the amino-terminal residues of PTH play a crucial role in stimulating the P1R to activate the cAMP and IP signaling pathways (Tregear, G. W., et al., *Endocrinology* 93:1349-1353 (1973); Takasu, H., et al., *Biochemistry* 38:13453-13460(1999)). Crosslinking and receptor mutagenesis studies have indicated that residues in the amino-terminal portion of PTH interact with the extracellular loops and extracellular ends of the seven transmembrane helices, which reside within the juxtamembrane region of the receptor (Bergwitz, C., et al., *J. Biol. Chem.* 271:26469-26472 (1996); Hoare, S. R. J., et al., *J. Biol. Chem* 276:7741-7753 (2001); Behar, V., et al., *J. Biol. Chem.* 275:9-17 (1999);

Shimizu, M., et al., *J. Biol. Chem.* 275:19456-19460 (2000); Luck, M. D., et al., *Molecular Endocrinology* 13:670-680 (1999)).

α-Helix Stabilizers

The first 34 amino acids of PTH and PTHrP contain sufficient information for high affinity P1R binding and potent induction of P1R-mediated signaling responses (Neer, R M, et al., *N. E. J. M* 344:1434-1441(2001)). Short N-terminal fragments of PTH, such as PTH(1-14) and PTH(1-11) exhibit extremely weak binding affinities (Kd>>100 μM) but are nonetheless capable of eliciting cAMP-signaling responses, albeit with potencies (EC50s≧100μM) that are substantially weaker than that of PTH(1-34)(EC50~2 nM) (Luck, M D et al., *Molecular Endocrinology* 13: 670-680(1999)). Recently, it has been discovered that a series of modified PTH(1-14) and PTH(1-11) analogs exhibit signaling potencies that are nearly, or even fully, equal to that of PTH(1-34)(Shimizu, M et al., *Endocrinology* 142: 3068-3074(2001); Shimizu, M. et al., *J. Biol. Chem.* 276: 490003-49012(2001); Shimizu, M. et al., *J. Biol. Chem.* 275: 21836-21843(2000)). One such type of a modifier is a lactam bridge, which is a side chain-to-side chain amide bridge formed between a basic lysine residue and an acidic aspartame or glutamate residue (Condon, S M. et al., *J. Am. Chem. Soc.* 122: 3007-3014 (2000)). Lactam bridge formation is a well-known method by which the bioactive conformation of peptides may be deduced (See Id.). Incorporation of lactam bridges between residues 13 and 17; 18 and 22; and 26 and 30 in human PTH (1-31) and (1-34) (hPTH) has shown bioactivity while retaining a helical conformation (see Id.). Additionally, these modifications of hPTH(1-31) and hPTH(1-34) suggest that an α-helix may be the preferred bioactive conformation for the N-terminal portion of PTH (Shimizu, N. et al., *J. Biol. Chem.* 276: 490003-49012 (2001)).

BRIEF SUMMARY OF THE INVENTION

The invention provides novel PTH polypeptide derivatives containing amino acid substitutions at selected positions in the polypeptides as well as derivatives containing lactam bridges between residues 6 and 10. The derivatives function as full, or nearly full, agonists of the PTH-1 receptor. Because of their unique properties, these polypeptides have utility as drugs for treating human diseases of the skeleton, such as osteoporosis.

In one aspect, the invention provides a method for treating mammalian conditions characterized by decreases in bone mass, said method comprising administering to a subject in need thereof an effective bone mass-increasing amount of a biologically active peptide consisting essentially of $X_{01}ValX_{02}GluIleX_{03}LeuMetHisX_{04}X_{05}X_{06}LysX_{07}LeuAsn$ SerMetGluArgValGlu TrpLeuArgLysLysLeuGlnAspVal-HisAsnTyr-$NH_2$ (SEQ. ID. NO.31) wherein $X_{01}$ is Gly, Ser, Ala or Aib; $X_{02}$ is Ala, Ser or Aib; $X_{03}$ is Asp, Glu or Lys; $X_{04}$ is Asp, Glu or Lys; $X_{05}$ is Arg, Har or Leu; $X_{06}$ is Ala or Gly; and $X_{07}$ is Trp or His. The invention is further drawn to treatments utilizing fragments of the peptide of SEQ. ID. NO. 31. The invention further encompasses methods of treatment utilizing pharmaceutically acceptable salts of the above-described peptides, and N- or C-derivatives of the peptides.

In another aspect, the invention provides a method for treating mammalian conditions characterized by decreases in bone mass, said method comprising administering to a subject in need thereof an effective bone mass-increasing amount of a biologically active peptide consisting essentially of $X_{01}ValX_{02}GluIleX_{03}LeuMetHisX_{04}X_{05}X_{06}LysX_{07}LeuAsn$ SerMetGluArgVal (SEQ. ID. NO. 32) wherein $X_{01}$ is Gly, Ser, Ala or Aib; $X_{02}$ is Ala, Ser or Aib; $X_{03}$ is Asp, Glu or Lys; $X_{04}$ is Asp, Glu or Lys; $X_{05}$ is Arg, Har or Leu; $X_{06}$ is Ala or Gly; and $X_{07}$ is Trp or His. The invention is further drawn to treatments utilizing fragments of the peptide of SEQ. ID. NO. 32. The invention further encompasses methods of treatment utilizing pharmaceutically acceptable salts of the above-described peptides, and N- or C-derivatives of the peptides.

In another aspect, the invention is directed to a method for treating mammalian conditions characterized by decreases in bone mass, said method comprising administering to a subject in need thereof an effective bone mass-increasing amount of a biologically active peptide consisting essentially of $X_{01}ValX_{02}GluIleX_{03}LeuMetHisX_{04}X_{05}X_{06}LysX_{07}$ (SEQ. ID. NO. 1) wherein $X_{01}$ is Gly, Ser, Ala or Aib; $X_{02}$ is Ala, Ser or Aib; $X_{03}$ is Asp, Glu or Lys; $X_{04}$ is Asp, Glu or Lys; $X_{05}$ is Arg, Har or Leu; $X_{06}$ is Ala or Gly; and $X_{07}$ is Trp or His.

In another aspect, the invention relates to a method for treating mammalian conditions characterized by decreases in bone mass, said method comprising to a subject in need thereof an effective bone-mass increasing amount of a biologically active peptide wherein paired $Glu^6/Lys^{10}$ or $Lys^6/Glu^{10}$ substitutions are introduced in otherwise non-constrained PTH(1-34), PTH(1-33), PTH(1-32), PTH(1-31), PTH(1-30), PTH(1-29), PTH(1-28), PTH(1-27), PTH(1-26), PTH(1-25), PTH(1-24), PTH(1-23), PTH(1-22), PTH(1-21), PTH(1-20), PTH(1-19), PTH(1-18), PTH(1-17), PTH(1-16), PTH(1-15), PTH(1-14), PTH(1-13), PTH(1-12), PTH(1-11), PTH(1-10), PTH(1-9) analog scaffolds. These analogs may exist in linear form, or an amide bond (lactam bridge) may be inserted between the carboxylate side chain group of the introduced glutamate reside and the amino side chain group of the introduced lysine residue, resulting in an α-helical conformation of the N-terminal domain of the PTH.

The invention is further drawn to treatments utilizing fragments of the peptide of SEQ. ID. NO. 1, in particular $X_{01}ValX_{02}GluIleX_{03}LeuMetHisX_{04}X_{05}X_{06}Lys$-amide (SEQ. ID. NO. 33), $X_{01}ValX_{02}GluIleX_{03}LeuMetHisX_{04}X_{05}X_{06}$-amide (part of SEQ. ID. NO.34), and $X_{01}ValX_{02}GluIleX_{03}LeuMetHisX_{04}X_{05}$-amide (part of SEQ. ID. NO. 35). The invention further encompasses methods of treatment utilizing pharmaceutically acceptable salts of the above-described peptides, and N- or C-derivatives of the peptides.

In addition, the invention is drawn to a method of treatment with a bone-mass increasing amount of a biologically active polypeptide consisting essentially of AlaValAlaGluIleX$_{01}$LeuMetHisGlnHarAlaLysTrp-amide (SEQ. ID. NO. 2) with paired $Glu^6/Lys^{10}$ or $Lys^6/Glu^{10}$, as well as $Asp^6/Lys^{10}$ or $Lys^6/Asp^{10}$ substitutions, and an amide bond between the carboxylate side chain group of the introduced glutamate residue and the amino side chain group of the introduced lysine residue; fragments thereof, containing amino acids 1-13, 1-12 and 1-11; pharmaceutically acceptable salts thereof; or N- or C-derivatives thereof.

Preferred embodiments of the biologically active peptide include: AlaValAlaGluIleGluLeuMetHisLysHarAlaLysTrp cyclized via a 6-10 lactam bridge (SEQ. ID. NO. 3), and AlaValAlaGluIleLysLeuMetHisLysHarAlaLysTrp cyclized via a 6-10 lactam bridge (SEQ. ID. NO. 4). It is contemplated that methods of treatment with fragments of the above mentioned peptides, containing amino acids 1-9, 1-10, 1-11, 1-12, or 1-13, are also embodiments of the present invention. The invention further encompasses pharmaceutically acceptable salts of the above-described peptides, and N- or C-derivatives of the peptides.

The invention also provides derivatives of rat PTH(1-34) (rPTH(1-34)) of the sequence AlaValSerGluIleGlnLeuMetHisAsnLeuGlyLysHisLeuAlaSer ValGluArgMetGlnTrpLeuArgLysLeuGlnAspValHisAsnPhe-amide (SEQ. ID. NO. 5), and of hPTH(1-34) having the sequence SerValSerGluIleGlnLeuMetHis AsnLeuGlyLysHisLeuAsnSerMetGluArgValGluTrpLeuArgLysLysLeuGlnAsp ValHisAsnPhe-amide (SEQ. ID. NO. 6). With regard to these derivatives, the invention is directed to treatment with a biologically active peptide consisting essentially of SerValSerGluIleX$_{01}$LeuMetHisX$_{02}$LeuGlyLysHisLeuAsnSerMet Glu ArgValGluTrpLeuArgLysLysLeuGlnAspValHisAsnTyr-amide, wherein X$_{01}$ is Lys, Glu, or Asp and X$_{02}$ is Glu, Asp or Lys (SEQ. ID. NO. 7).

This invention also provides methods of treatment with a bone-mass increasing amount of pharmaceutical compositions comprising any of the PTH derivatives described herein and a pharmaceutically acceptable excipient and/or a pharmaceutically acceptable solution such as saline or a physiologically buffered solution.

In one aspect, the invention is directed to administering to a subject in need thereof an effective bone mass-increasing amount of a pharmaceutical composition comprising the biologically active peptide having the sequence of SEQ. ID. NO. 1, SEQ. ID. NO. 31, or any of the above peptides, and a pharmaceutically acceptable carrier.

In another aspect, the invention is directed to a method of making SEQ. ID. NO. 1, SEQ. ID. NO. 31, or any of the above peptides, wherein the peptide is synthesized by solid phase synthesis, liquid phase synthesis, or solution phase synthesis.

In another aspect, the invention is directed to a method of making SEQ. ID. NO. 1, SEQ. ID. NO. 31, or any of the above peptides, wherein the peptide is protected by FMOC.

This invention also provides a method for treating mammalian conditions characterized by decreases in bone mass, the method of which comprises administering to a subject in need thereof an effective bone mass-increasing amount of a biologically active PTH polypeptide derivative. A preferable embodiment of the invention is drawn to conditions such as osteoporosis. The types of osteoporosis include, but are not limited to old age osteoporosis and postmenopausal osteoporosis.

In another aspect, the invention is directed to a method for treating mammalian conditions characterized by decreases in bone mass, the method comprising administering to a subject in need thereof an effective bone mass-increasing amount of a biologically active peptide of having the sequence of SEQ. ID. NO. 1, SEQ. ID. NO. 31, or any of the above peptides and a pharmaceutically acceptable carrier. Additional preferable embodiments include using an effective amounts of the polypeptide of about 0.01 µg/kg/day to about 1.0 µg/kg/day wherein the polypeptide is administered parenterally, subcutaneously or by nasal insufflation.

This invention also provides a method for determining rates of bone reformation, bone resorption and/or bone remodeling comprising administering to a patient an effective amount of a labeled PTH polypeptide, such as for example, a peptide having the sequence of SEQ. ID. NO. 1, SEQ. ID. NO. 31, or derivatives thereof and determining the uptake of the peptide into the bone of the patient. The peptide may be labeled with a label selected from the group consisting of: radiolabel, flourescent label, bioluminescent label, or chemiluminescent label. In a preferable embodiment the radiolabel is $^{125}$I or $^{99m}$Tc.

DETAILED DESCRIPTION OF THE INVENTION

Definitions

Figure 1:
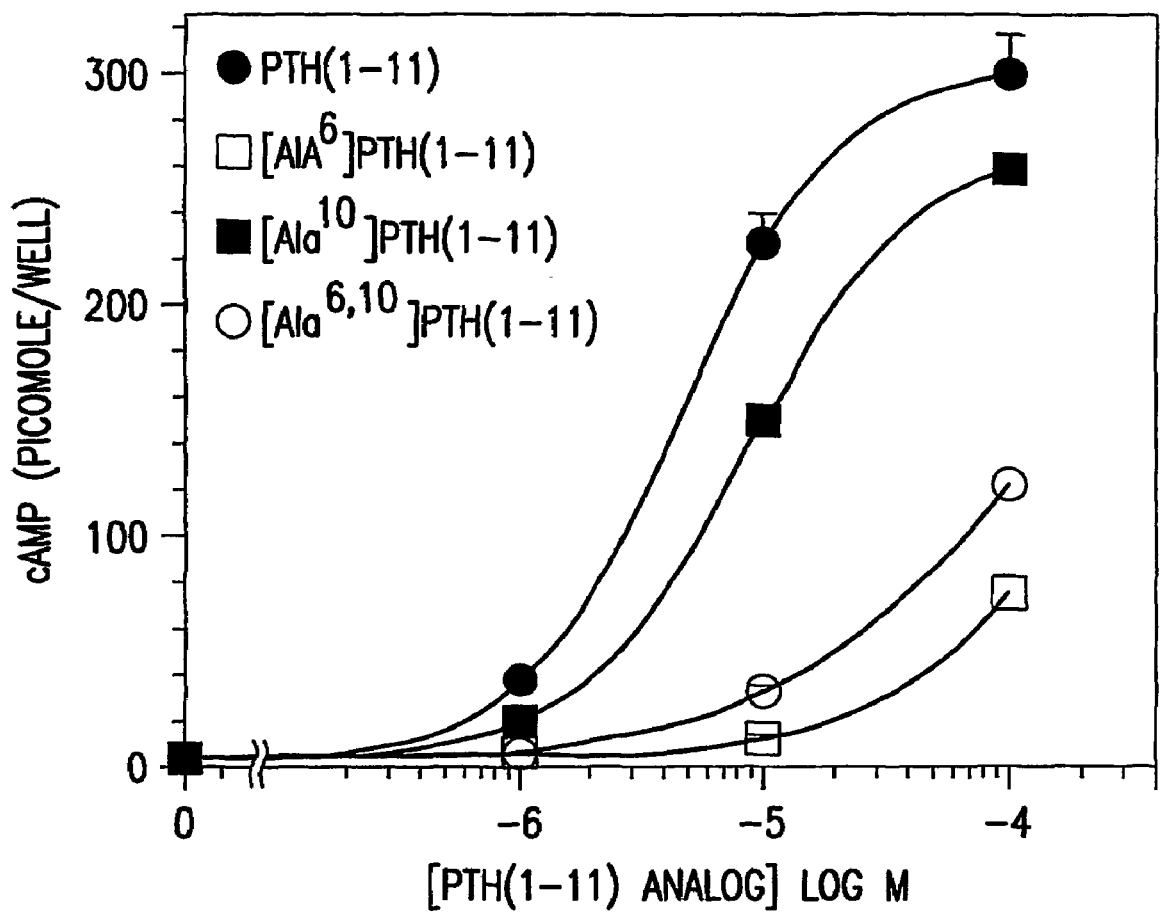
FIG. 1. Effects of Gln and Ala substitutions at positions 6 and 10 of PTH(1-11) analogs on cAMP-stimulating potency in HKRK-B7. The parent peptide PTH(L-11)(AVAEIQLM-HQR-amide) (SEQ. ID. NO. 8) and analogs of that peptide containing the substitutions at positions 6 and/or 10 indicated by the symbol key, were evaluated for cAMP-stimulating potency in HKRK-B7 cells.
Figure 2B:
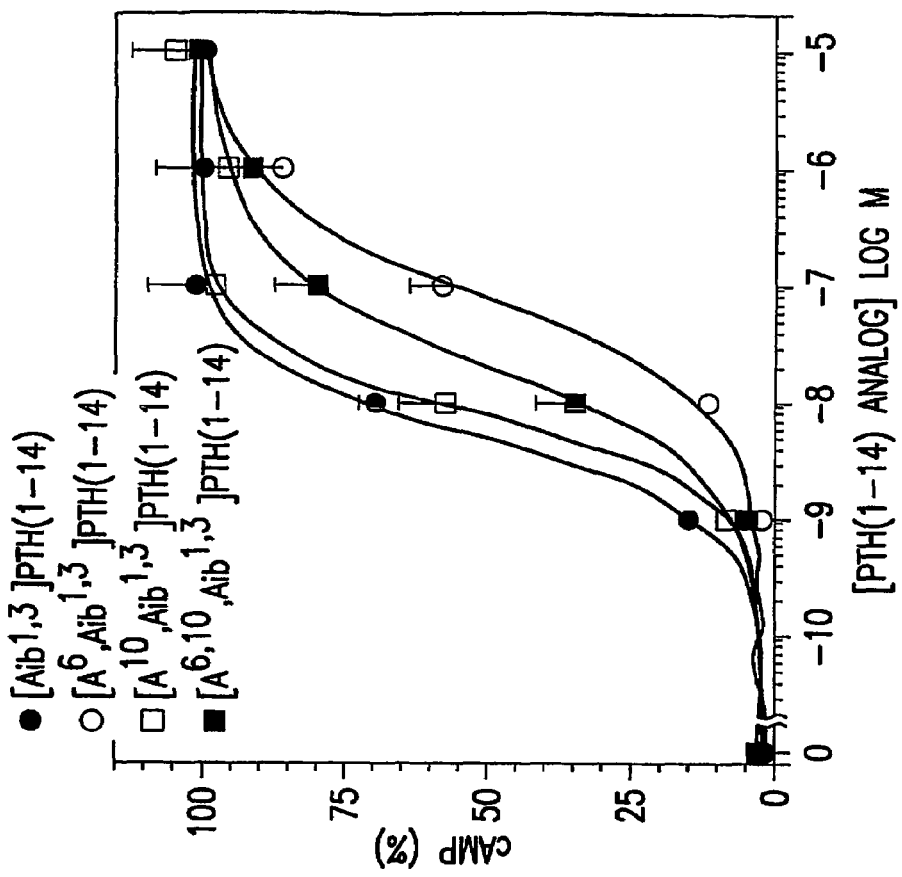
FIG. 2. Effects of substitutions at positions 6 and 10 in PTH (1-11) and PTH(1-14) on analog potency in LDElNt-2 cells. A) The parent peptide PTH(1-11)(AlaValAlaGluIleGlnLeuMetHisGlnHar-amide) (SEQ. ID. NO. 8) and analogs thereof substituted at position 6 and/or 10, as indicated by the symbol key, were evaluated for cAMP-stimulating potency in LdelNt-2 cells, an LLC-PK1-derived cell line that expresses, via stable transfection, P1R-DelNt, a P1R construct that lacks most of the amino-terminal extracellular domain. B) The conformationally constrained peptide [Aib$^{1,3}$]PTH(1-14) (AibValAibGluIleGlnLeuMetHisGlnHarAlaLysTrp-amide) (SEQ. ID. NO.9) and analogs thereof substituted at positions 6 and/or 10, as indicated in the symbol key were evaluated as in panel A. The data in panel A are expressed as a percent of the maximum response observed in each experiment for PTH (1-11), which was 113±4 pM of cAMP per well (n=3); the corresponding basal cAMP level was 2.0±0.3 pM per well. The data in panel B are expressed as a percent of the maximum response observed for PTH(1-14), which was 108±3 pM of cAMP per well (n=3); the corresponding basal cAMP level was 1.8±0.5 pM per well.
Figure 2A:
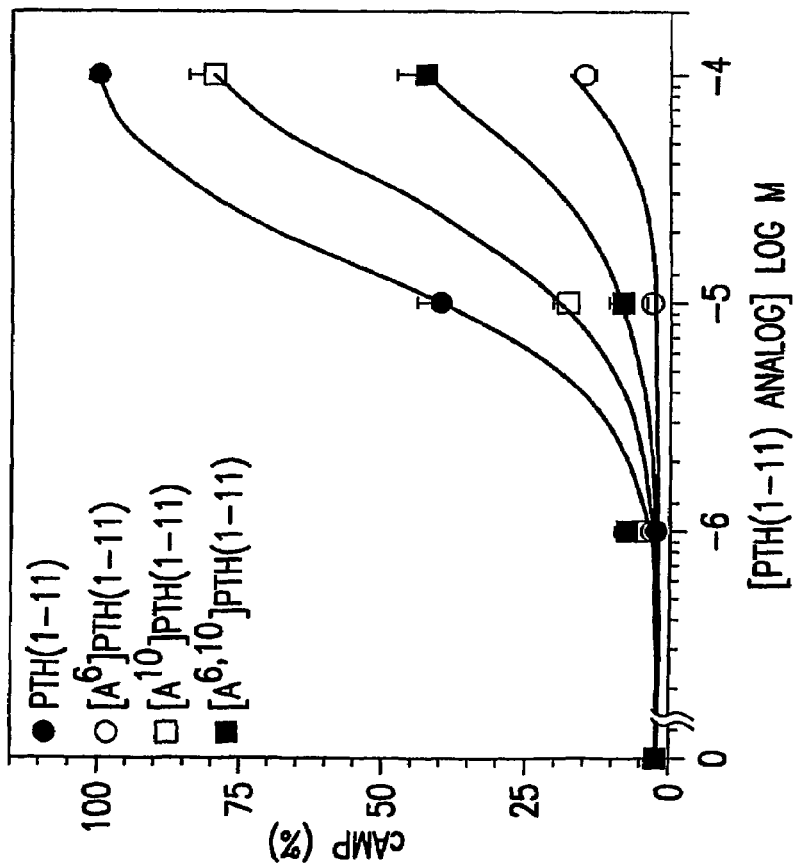
Figure 3A:
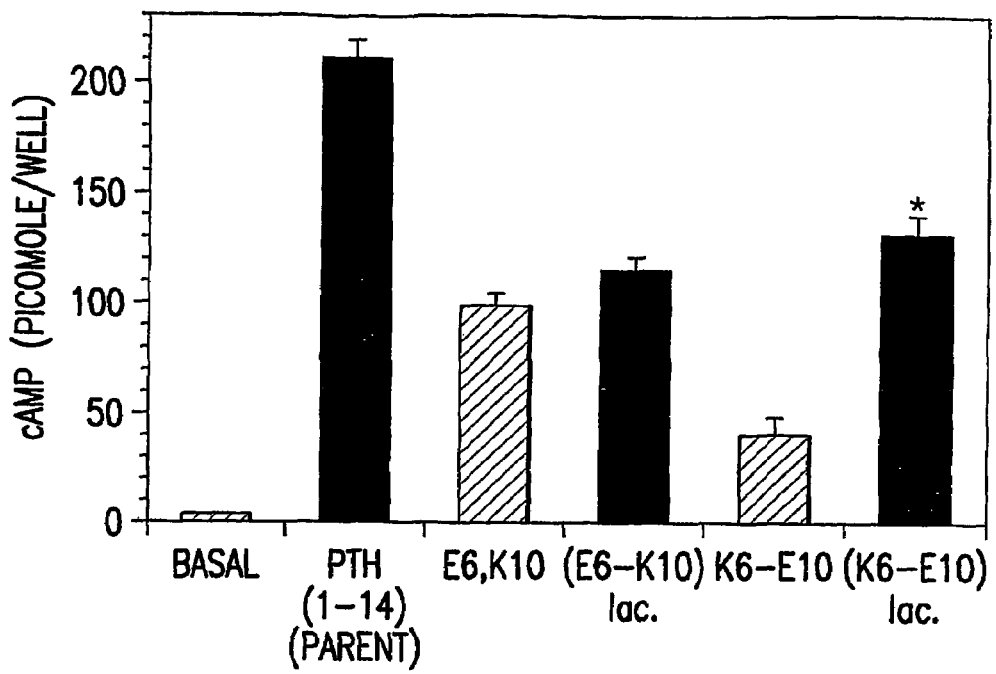
FIG. 3. Effect of a lactam bridge between positions 6 and 10 in PTH(1-14) analogs on cAMP-stimulating potency in HKRK-B28 cells. A) The peptide [M]PTH(1-14)(AlaValAlaGluIleGlnLeuMetHisGlnHarAlaLysTrp-amide) (SEQ. ID. NO. 11) and analogs thereof containing Glu or Lys substitutions at positions 6 and 10, for which the side chains were either unmodified or were covalently linked in a lactam bridge (lac.), were evaluated at a dose of 10 µM for the capacity to stimulate cAMP accumulation via the wild-type P1R expressed, via stable transfection, in HKRK-B28 cells. The asterisk indicates that the response elicited by [(Lys$^6$, Glu$^{10}$)lac.]PTH(1-14) (SEQ. ID. NO. 26) was significantly (P<0.0001) greater than that elicited by the linear control [Lys$^6$,Glu$^{10}$]PTH(1-14)(SEQ. ID. NO. 25). B) The PTH(1-14) analogs containing Lys$^6$/Glu$^{10}$ substitutions in either linear or lactam bridged form, were evaluated at varying doses for the capacity to stimulate cAMP accumulation in HKRK-B28 cells. The data in panel B are expressed as a percent of the maximum response observed for PTH(1-14), which was 359±52 picomoles of cAMP per well (n=3); the corresponding basal cAMP level was 6±1 picomoles per well. Peptides and corresponding symbols are defined in the key.
Figure 3B:
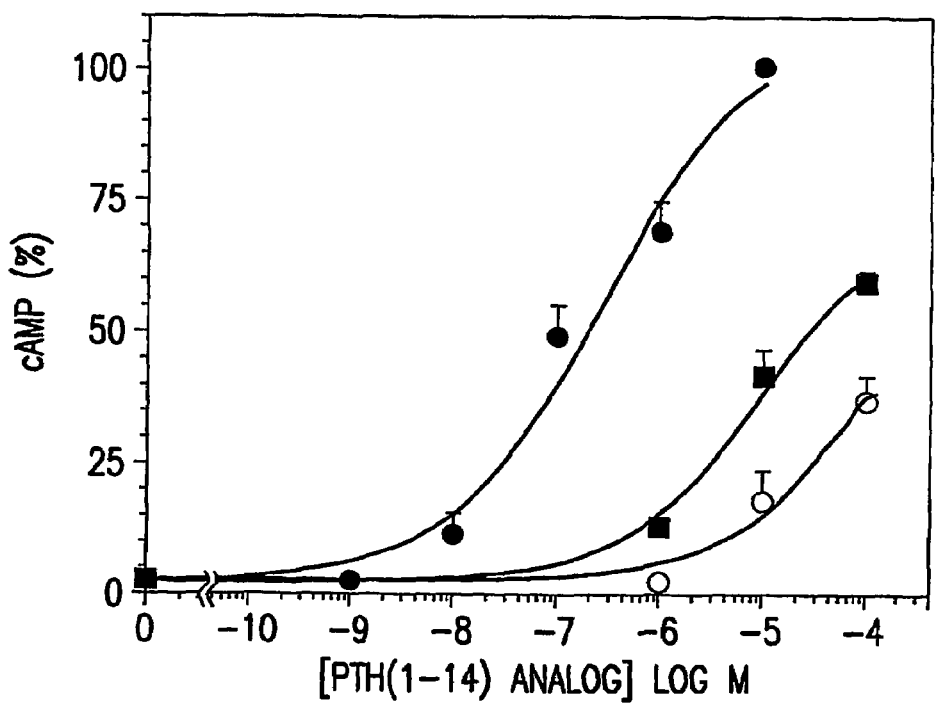
Figure 4B:
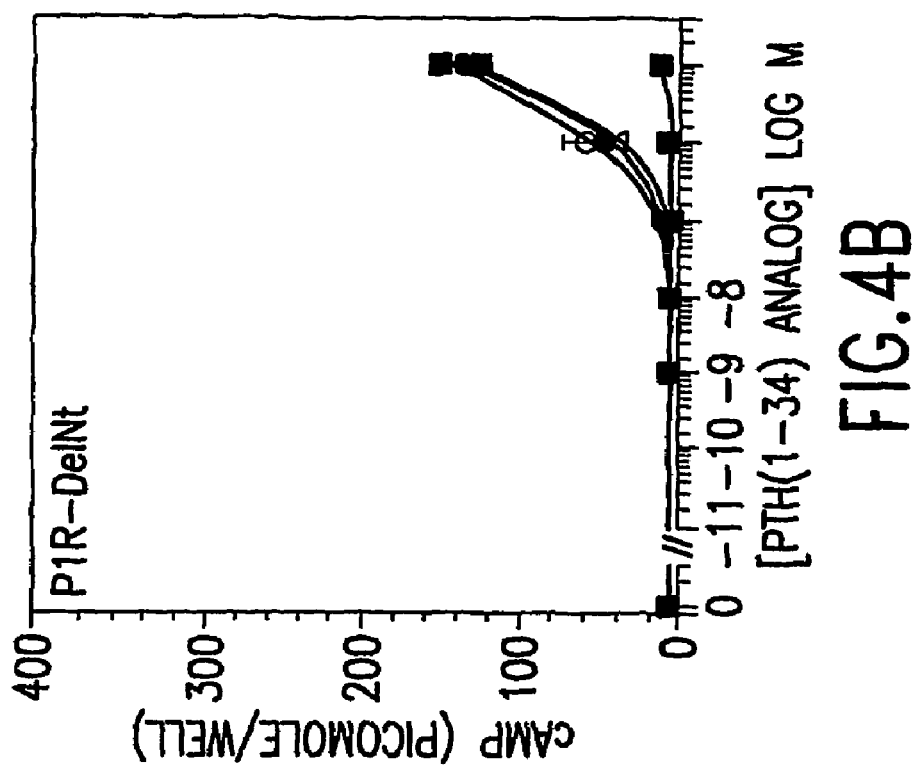
FIG. 4. Effects of substitutions at positions 6 and 10 in PTH(1-34) analogs on cAMP-stimulating potency in COS-7 cells. The peptide PTH(1-34)([Tyr$^{34}$]hPTH(1-34)amide) (SEQ. ID. NO. 10) and analogs thereof containing substitutions at positions 6 and/or 10, as indicated by the symbol key, were evaluated for cAMP-stimulating potencies in COS-7 cells expressing, via transient transfection, either the wild-type P1R(A) or P1R-DelNt(13) (note that the potencies of the analogs on P1r-DelNt are much weaker than those seen on the wild-type P1R; a result that reflects the importance of the N domain of the receptor in mediating binding interactions for PTH(1-34) peptides.
Figure 4A:
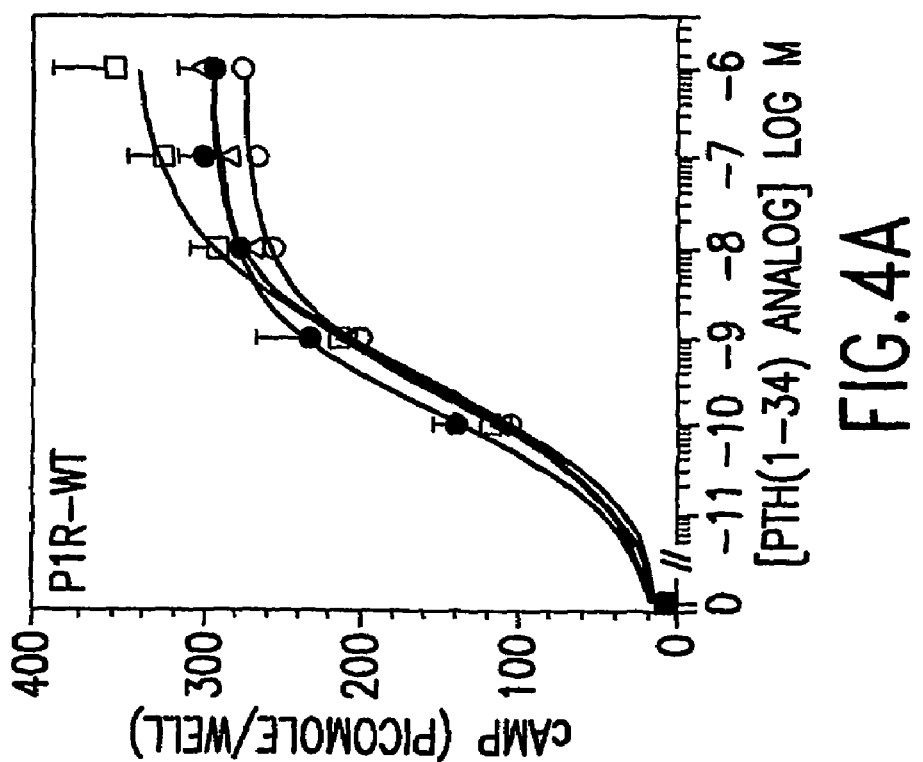

Amino Acid Sequences: The amino acid sequences in this application use either the single letter or three letter designations for the amino acids. These designations are well known to one of skill in the art and can be found in numerous readily available references, such as for example in Cooper, G. M, *The Cell* 1997, ASM Press, Washington, D.C. or Ausubel et al., *Current Protocols in Molecular Biology,* 1994. Where substitutions in a sequence are referred to, for example, as Ser-3-->Ala or [Ala$^3$]peptide, this means that the serine in the third position from the N-terminal end of the polypeptide is replaced with another amino acid, Alanine in this instance.

In the present application [M]PTH(1-14) is defined as [Ala$^{1,3,12}$,Gln$^{10}$,Har$^{11}$,Trp$^{14}$]PTH(1-14)amide (SEQ. ID. NO. 11), which is an analog of human PTH(1-14) (SEQ. ID. NO.12). [M]PTH(1-11) is defined as [Ala$^{1,3}$,Gln$^{10}$,Har$^{11}$]PTH(11)amide (SEQ. ID. NO. 12).

In the present application, "Aib" refers to α-aminoisobutyric acid; "Har" refers to homoarginine; "Nle" refers to norleucine; Deg refers to diethylglycine; and other amino acids are in either the conventional one- or three-letter codes.

Biological Activity of the Protein: This expression refers to any biological activity of the polypeptide. Examples of these activities include, but are not limited to metabolic or physiologic function of compounds of a peptide having the sequence of SEQ. ID. NO. 1 or derivatives thereof, including similar activities or improved activities, or those activities with decreased undesirable side-effects. Also included are antigenic and immunogenic activities of the above-described compounds.

Derivative or Functional Derivative: The term "derivative" or "functional derivative" is intended to include "variants," the "derivatives," or "chemical derivatives" of the PTH molecule. A "variant" of a molecule such as for example, a compound of a peptide having the sequence of SEQ. ID. NO. 1 or derivative thereof is meant to refer to a molecule substantially similar to either the entire molecule, or a fragment thereof. An "analog" of a molecule such as for example, a compound having the sequence of SEQ. ID. NO. 1 or derivative thereof is meant to refer to a non-natural molecule substantially similar to either the peptide having the sequence of SEQ. ID. NO. 1 molecules or fragments thereof.

PTH derivatives contain changes in the polypeptide relative to the native PTH polypeptide of the same size. The sequence of the native human PTH(1-14) polypeptide is Ser-ValSerGluIleGlnLeuMetHisAsnLeuGlyLysHis-amide (SEQ. ID. NO. 36), or native rat PTH (1-14) is AlaValSer-GluIleGlnLeuMetHisAsn LeuGlyLysHis-amide (part of SEQ. ID. NO. 37).

A molecule is said to be "substantially similar" to another molecule if the sequence of amino acids in both molecules is substantially the same, and if both molecules possess a similar biological activity. Thus, two molecules that possess a similar activity, may be considered variants, derivatives, or analogs as that term is used herein even if one of the molecules contains additional amino acid residues not found in the other, or if the sequence of amino acid residues is not identical. PTH derivatives, however, need not have substantially similar biological activity to the native molecule. In some instances PTH derivatives have substantially different activity than the native PTH. For example, a derivative may be either an antagonist or an agonist of the PTH receptor.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Fragment: A "fragment" of a molecule such as for example, $X_{01}$ValX$_{02}$GluIleX$_{03}$LeuMetHisX$_{04}$X$_{05}$X$_{06}$Lys-amide (1-13) (SEQ. ID. NO. 33) or derivative thereof is meant to refer to any polypeptide subset of these molecules.

Fusion protein: As used herein, a "fusion protein" is a protein comprising compounds such as for example, $X_{01}$ValX$_{02}$GluIleX$_{03}$LeuMetHisX$_{04}$X$_{05}$X$_{06}$LysX$_{07}$-amide (SEQ. ID. NO. 1), or derivatives thereof, either with or without a "selective cleavage site" linked at its N-terminus, which is in turn linked to an additional amino acid leader polypeptide sequence.

Polypeptide: Polypeptide and peptide are used interchangeably. The term polypeptide refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids and include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched and they may be cyclic, with or without branching. Cyclic, branched and branched cyclic polypeptides may result from post-translational modifications or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties,* 2nd Ed., T. E. Creighton, W. H. Freeman and Company, New York, 1993 and Wold, F., Posttranslational Protein Modifications: Perspectives and Prospects, pgs. 1-12 in *Posttranslational Covalent Modification of Proteins,* B. C. Johnson, Ed., Academic Press, New York, 1983; Seifter et al., "Analysis for protein modifications and nonprotein cofactors", *Methods in Enzymol.* 182:626-646 (1990) and Rattan et al., "Protein Synthesis: Posttranslational Modifications and Aging", *Ann NY Acad Sci* 663:48-62 (1992).

PTH Analogs—Structural and Functional Properties

α-aminoisobutyric acid (Aib) and α,α-disubstituted amino acids distinct from Aib were introduced into short N-terminal PTH peptide analogs. The numerous NMR studies of PTH(1-34) analogs, performed in a variety of polar or non-polar solvents, have generally indicated two domains of secondary structure: a stable C-terminal helix extending approximately from Ser-17 to Val-31, and a shorter and less stable amino-terminal helix, extending variably from Ser-3 to Lys-13, the two domain being connected by a bend or turn region (Marx, U. C., et al., *Biochem. Biophys. Res. Commun.* 267:213-220 (2000); Chen, Z., et al., *Biochemistry* 39:12766-12777 (2000); Marx, U. C., et al, *J. Biol. Chem.* 270:15194-15202 (1995); Marx, U. C., et al., *J. Biol. Chem.* 273:4308-4316 (1998); Pellegrini, M., et al., *Biochemistry* 37:12737-12743 (1998); Gronwald, W., et al., *Biol. Chem. Hoppe Seyler* 377: 175-186 (1996); Barden, J. A., and Kemp, B. E., *Biochemistry* 32:7126-7132 (1993)). The recent crystallographic study of PTH(1-34) indicated a continuous α-helix extending from Ser-3 to His-32 and containing only a slight 15° bend at the midsection. However, NMR data indicates that the N-terminal α-helix is relatively weak. Helix-stabilizing modifications, such as the introduction of Aib residues, offer significant benefits in terms of peptide potency, and result in short peptides (≦14 amino acids) with activity comparable to PTH (1-34).

Described herein are novel "minimized" variants of PTH that are small enough to be deliverable by simple non-injection methods. The variants of the present invention contain substitutions in the first 14 amino acids of the polypeptide. The new polypeptides correspond to the 1-14, 1-13, 1-12, 1-11, 1-10, and 1-9 amino acid sequence of the mature PTH polypeptide. The shorter variants (≦PTH1-14) have a molecular weight of less than 2,000 daltons.

As protein products, compounds described herein are amenable to production by the techniques of solution- or solid-phase peptide synthesis. The solid phase peptide synthesis technique, in particular, has been successfully applied in the production of human PTH and can be used for the production of these compounds (for guidance, see Kimura et al., supra, and see Fairwell et al., *Biochem.* 22:2691 (1983)). Success with producing human PTH on a relatively large scale has been reported by Goud et al., in *J. Bone Min. Res.* 6(8):781 (1991). The synthetic peptide synthesis approach generally entails the use of automated synthesizers and appropriate resin as solid phase, to which is attached the C-terminal amino acid of the desired compounds of peptides having the sequence of SEQ. ID. NO. 31, SEQ. ID. NO. 1, or derivatives thereof. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of such as for example, SEQ. ID. NO. 31, SEQ. ID. NO. 1, and derivatives thereof which incorporate amino acids that are not genetically encoded, such as Aib.

Substituents may be attached to the free amine of the N-terminal amino acid of compounds of the present invention standard methods known in the art. For example, alkyl groups, e.g., $C_{1-12}$ alkyl, are attached using reductive alkylation. Hydroxyalkyl groups, e.g. $C_{1-12}$ hydroxyalkyl, are also attached using reductive alkylation wherein the free hydroxy group is protected with a t-butyl ester. Acyl groups, e.g., $COE_1$, are attached by coupling the free acid, e.g., $E_1COOH$, to the free amino of the N-terminal amino acid. Additionally, possible chemical modifications of the C-terminal end of the polypeptide are encompassed within the scope of the invention. These modifications may modify binding affinity to the receptor.

Also contemplated within the scope of this invention are those compounds such as for example, a peptide having the sequence of SEQ. ID. NO. 1, SEQ. ID. NO. 31, and derivatives thereof with altered secondary or tertiary structure, and/or altered stability, which still retain biological activity. Such derivatives might be achieved through lactam cyclization, disulfide bonds, or other means known to a person of ordinary skill in the art. Lactam bridge modifications between glutamic acid and lysine side chains may be prepared using an orthogonal protection strategy with allyl-protected amino acids, as is well known in the art (Blackburn, C., and Kates, S. A., *Methods Enzymol* 289: 175-198 (1997). A preferable embodiment of the invention is drawn to any of the above recited polypeptides, wherein the polypeptide contains a C-terminal amide. However, it is contemplated that all peptides of the current invention may also be used without the incorporation of a C-terminal amide.

Utility and Administration of Compounds of the Invention

Compounds of the invention or derivatives thereof have multiple uses. These include, inter alia, agonists or antagonists of the PTH receptor, prevention and treatment of a variety of mammalian conditions manifested by loss of bone mass, diagnostic probes, antigens to prepare antibodies for use as diagnostic probes and even as molecular weight markers. Being able to specifically substitute one or more amino acids in the PTH polypeptide permits construction of specific molecular weight polypeptides.

In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. Finally, the compounds of this invention are also indicated for the prophylaxis and therapeutic treatment of hypoparathyroidism.

In general, compounds of the present invention, or salts thereof; are administered in amounts between about 0.01 and 1 μg/g body weight per day, preferably from about 0.07 to about 0.2 μg/kg body weight per day. For a 50 kg human female subject, the daily dose of biologically active compound is from about 0.5 to about 50 μgs, preferably from about 3.5 to about 10 μgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. For example, this dosage may be delivered in a conventional pharmaceutical composition by nasal insufflation.

The selection of the exact dose and composition and the most appropriate delivery regimen will be influenced by, inter alia, the pharmacological properties of the selected compounds of the invention, the nature and severity of the condition being treated, and the physical condition and mental acuity of the recipient.

Representative preferred delivery regimens include, without limitation, oral, parenteral, subcutaneous, transcutaneous, intramuscular and intravenous, rectal, buccal (including sublingual), transdermal, and intranasal insufflation.

Pharmaceutically acceptable salts retain the desired biological activity of the compounds of the invention without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like. Pharmaceutically acceptable buffers include but are not limited to saline or phosphate buffered saline. Also included in these solutions may be acceptable preservative known to those of skill in the art.

A further aspect of the present invention relates to pharmaceutical compositions comprising as an active ingredient compounds of the invention or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for the most preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987.

Like PTH, the PTH variants may be administered in combination with other agents useful in treating a given clinical condition. When treating osteoporosis and other bone-related disorders for example, the PITH variants may be administered in conjunction with a dietary calcium supplement or with a vitamin D analog (see U.S. Pat. No. 4,698,328). Alternatively, the PTH variant may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

PTH Analog Receptor-Signaling Activities

A crucial step in the expression of hormonal action is the interaction of hormones with receptors on the plasma membrane surface of target cells. The formation of hormone-receptor complexes allows the transduction of extracellular signals into the cell to elicit a variety of biological responses.

Polypeptides described herein can be screened for their agonistic or antagonistic properties using the cAMP accumulation assay. Cells expressing PTH-1 receptor on the cell surface are incubated with native PTH(1-84) (SEQ. ID. NO. 13) for 5-60 minutes at 37° C., in the presence of 2 mM IBMX (3-isobutyl-1-methyl-xanthine, Sigma, St. Louis, Mo.). Cyclic AMP accumulation is measured by specific radioimmunoassay. A compound that competes with native PTH ((1-84) or PTH((1-34)(SEQ. ID. NO. 6) for binding to the PTH-1 receptor, and that inhibits the effect of native PTH(1-84) or PTH(1-34) on cAMP accumulation, is considered a competitive antagonist. Such a compound would be useful for treating hypercalcemia.

Conversely, a PTH analog described herein or a derivative thereof that does not compete with native PTH(1-84) or PTH (1-34) for binding to the PTH-1 receptor, but which still prevents native PTH(1-84) or PTH(1-34) activation of cAMP accumulation (presumably by blocking the receptor activation site) is considered a non-competitive antagonist. Such a compound would be useful for treating hypercalcemia.

The compounds described herein that compete with native PTH(1-84) or PTH(1-34)) for binding to the PTH-1 receptor, and which stimulates cAMP accumulation in the presence or absence of native PTH(1-84) or PTH(1-34) are competitive agonists. A compound that does not compete with native PTH(1-84) or PTH(1-34) for binding to the PTH-1 receptor but which is still capable of stimulating cAMP accumulation in the presence or absence of native PTH(1-84) or PTH(1-34), or which stimulates a higher cAMP accumulation than that observed by a compound of the invention or a derivative thereof alone, would be considered a non-competitive agonist.

Therapeutic Uses of PTH Analogs

Some forms of hypercalcemia and hypocalcemia are related to the interaction between PTH and PTHrP and the PTH-1 and receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma. Hypocalcemia, a condition in which the serum calcium level is abnormally low, may result from a deficiency of effective PTH, e.g., following thyroid surgery.

By "agonist" is intended a ligand capable of enhancing or potentiating a cellular response mediated by the PTH-1 receptor. By "antagonist" is intended a ligand capable of inhibiting a cellular response mediated by the PTH-1 receptor. Whether any candidate "agonist" or "antagonist" of the present invention can enhance or inhibit such a cellular response can be determined using art-known protein ligand/receptor cellular response or binding assays, including those described elsewhere in this application.

In accordance with yet a further aspect of the invention, there is provided a method for treating a medical disorder that results from altered or excessive action of the PTH-1 receptor, comprising administering to a patient therapeutically effective amount of a compound of the invention or a derivative thereof sufficient to inhibit activation of the PTH-1 receptor of said patient.

In this embodiment, a patient who is suspected of having a disorder resulting from altered action of the PTH-1 receptor can be treated using compounds of the invention or derivatives thereof of the invention which are a selective antagonists of the PTH-1 receptor. Such antagonists include compounds of the invention or derivatives thereof of the invention which have been determined (by the assays described herein) to interfere with PTH-1 receptor-mediated cell activation or other derivatives having similar properties.

To administer the antagonist, the appropriate compound of the invention or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides adequate inhibition of a compound of the invention or a derivative thereof binding to the PTH-1 receptor. Typical dosage would be 1 ng to 10 mg of the peptide per kg body weight per day.

In accordance with yet a further aspect of the invention, there is provided a method for treating osteoporosis, comprising administering to a patient a therapeutically effective amount of a compound of the invention or a derivative thereof, sufficient to activate the PTH-1 receptor of said patient. Similar dosages and administration as described above for the PTH/PTHrP antagonist, can be used for administration of a PTH/PTHrP agonist, e.g., for treatment of conditions such as osteoporosis, other metabolic bone disorders, and hypoparathyroidism and related disorders.

It will be appreciated by those skilled in the art that the invention can be performed within a wide range of equivalent parameters of composition, concentration, modes of administration, and conditions without departing from the spirit or scope of the invention or any embodiment thereof.

Having now fully described the invention, the same will be more readily understood by reference to specific examples which are provided by way of illustration, and are not intended to be limiting of the invention, unless herein specified.

EXAMPLES

The following protocols and experimental details are referenced in the examples that follow.

Example 1

Materials and Methods

Peptides. Each peptide utilized in this study contained a free amino acid terminus and a carboxamide at the C-terminus. Peptides were prepared on automated peptide synthesizers (model 430A PE, Applied Biosystems, Foster City, Calif., or Model 396 MBS Advanced Chem Tect, Louisville, Ky.) using FMOC main-chain protecting group chemistry, HBTU/HOBt/DIEA (1:1:2 molar ratio) for coupling reactions, and TFA-mediated cleavage/sidechain-deprotection (MGH Biopolymer Synthesis Facility, Boston, Mass.). All peptides were desalted by adsorption on a C18-containing cartridge, and purified further by HPLC. The dry peptide powders were reconstituted in 10 mM acetic acid and stored at $-80°$ C. The purity, identity, and stock concentration for each peptide was secured by analytical HPLC, Matrix-assisted laser desorption/ionization (MALDI) mass spectrometry and amino acid analysis. Radiolabeling of [M]PTH(1-21)(SEQ. ID. NO. 4) and [Aib$^{1,3}$,M]PTH(1-21)(SEQ. ID. NO. 15) was performed using $^{125}$I-Na (2,200 Ci/mmol, NEN) and chloramine-T; the resultant radioligands were purified by HPLC.

Cell Culture. The cell line HKRK-B28 (Takasu, H., et al., *J. Bone Miner. Res.* 14:11-20 (1999)) was derived from the porcine kidney cell line, LLC-PK$_1$ by stable transfection with plasmid DNA encoding the full-length P1R and expresses ~280,000 receptors per cell. These cells, as well as COS-7 cells and SaOS-2-B10 cells, were cultured at 27° C. in T-75 flasks (75 mm$^2$) in Dulbecco's modified Eagle's medium (DMEM) supplemented with fetal bovine serum (10%), penicillin G (20 units/ml), streptomycin sulfate (20 µg/ml) and amphotericin B (0.05 µg/ml) in a humidified atmosphere containing 5% $CO_2$. Stock solutions of EGTA/trypsin and antibiotics were from GIBCO; fetal bovine serum was from Hyclone Laboratories (Logan, Utah). COS-7 cells sub-cultured in 24-well plates were transfected with plasmid DNA (200 ng per well) encoding the wild-type human P1R or truncated human P1R deleted for residues (24-181) (Shimizu, M., et al., *J. Biol. Chem.* 275:21836-21843 (2000)) that was purified by cesium chloride/ethidium bromide density gradient centrifugation, and FuGENE 6 transfection reagent (Roche Indianapolis Ind.) according to the manufacturer's recommended procedure. All cells, in 24-well plates, were treated with fresh media and shifted to 33° C. for 12 to 24 h prior to assay.

cAMP Stimulation. Stimulation of cells with peptide analogs was performed in 24-well plates. Cells were rinsed with 0.5 mL of binding buffer (50 mM Tris-HCl, 100 mM NaCl, 5 mM KCl, 2 mM $CaCl_2$, 5% heat-inactivated horse serum, 0.5% fetal bovine serum, adjusted to pH 7.5 with HCl) and treated with 200 μL of cAMP assay buffer (Delbecco's modified Eagle's medium containing 2 mM 3-isobutyl-1-methylxanthine, 1 mg/mL bovine serum albumin, 35 mM Hepes-NaOH, pH 7.4) and 100 μL of binding buffer containing varying amounts of peptide analog (final volume=300 μL). The medium was removed after incubation for 30 to 60 minutes at room temperature, and the cells were frozen on dry ice, lysed with 0.5 mL 50 mM HCl, and refrozen (~80° C.). The cAMP content of the diluted lysate was determined by radioimmunoassay. The $EC_{50}$ response values were calculated using nonlinear regression (see below).

FMOC. (Fluorenylmethoxycarbonyl group) A group used for linkage to amino groups for the purpose either of forming fluorescent amino-acid derivatives that can readily be detected after column chromatography, or to protect the amino groups of amino acids or nucleotides while other functional groups are undergoing reaction. Reagents useful for introducing the group are 9-fluorenylmethyl chloroformate and 9-fluorenyl-methyl succinimidyl carbonate.

Competition Binding. Binding reactions were performed with HKPK-B28 cells or in COS-7 cells in 24-well plates. The cells were rinsed with 0.5 mL of binding buffer, and then treated successively with 100 μL binding buffer, 100 μL of binding buffer containing various amounts of unlabeled competitor ligand, and 100 μL of binding buffer containing ca. 100,000 cpm of $^{125}$I-[M]PTH(1-21)(SEQ. ID. NO. 16) or $^{125}$I-[Aib$^{1,3}$,M]PTH(1-21)(SEQ. ID. NO. 17) (ca. 26 fmol; final volume=300 μL). Incubations were 4 to 6 h at 4° C., at which time near equilibrium conditions were attained. Cells were then placed on ice, the binding medium was removed, and the monolayer was rinsed three times with 0.5 mL of cold binding buffer. The cells were subsequently lysed with 0.5 mL 5N NaOH and counted for radioactivity. For each tracer and in each experiment, the non-specific binding was determined as the radioactivity that bound in the presence of the same unlabeled peptide at a concentration of 1 μM, and was ~1% of total radioactivity added for each tracer. The maximum specific binding ($B_0$) was the total radioactivity bound in the absence of competing ligand, corrected for nonspecific binding, and for each tracer, ranged from 8% to 20% of the total radioactivity added. Nonlinear regression was used to calculate binding $IC_{50}$ values (see below). Scatchard transformations of homologous competition binding data derived from studies with 26 fmol of $^{125}$I-[Aib$^{1,3}$,M]PTH(1-21) (SEQ. ID. NO. 17) were employed for estimations of apparent equilibrium dissociation constant ($k_{Dapp}$s) and total number of ligand binding sites ($B_{max}$), assuming a single class of binding sites and equal affinities of the iodinated and non iodinated ligand.

Stimulation of Inositol Phosphate Production. COS-7 cells transfected as above with P1R-WT were treated with serum-free, inositol-free DMEM containing 0.1% bovine serum albumin and [$^3$H]myo-inositol (NEN, Boston, Mass.) (2 μCi/mL) for 16 h prior to assay. At the time of the assay, the cells were rinsed with binding buffer containing LiCl (30 mM) and treated with the same buffer with or without a PTH analog. The cells were then incubated at 37° C. for 40 min, after which the buffer was removed and replaced by 0.5 mL of ice cold 5% trichloroacetic acid solution. After 3 h on ice, the lysate was collected and extracted twice with ethyl ether. The lysate was then applied to an ion exchange column (0.5 mL resin bed) and the total inositol phosphates were eluted as described previously (Berridge, M. J., et al., *Biochem. J.* 212:473-482 (1983)), and counted in liquid scintillation cocktail.

Inhibition of Chondrocyte Differentiation in Embryonic Mouse Metatarsals. Metatarsals from embryonic day (E) 15.5 mouse embryos were excised and cultured in a 37° C. humidified incubator (5% $CO_2$) in serum-free αMEM media in 24 well plates. Sixteen hours later, a PTH analog or vehicle was added, and the samples were incubated for an additional 48 h in 37° C. with peptide or vehicle added again at the 24 h time point. At the end of the 64 h incubation period, the samples were fixed with 10% formalin/phosphate-buffered saline, then directly visualized on a dissecting microscope using white light. Sections were processed for in-situ hybridization analysis using $^{35}$S-labeled riboprobes specific for collagen type X mRNA, a developmental marker gene expressed only in hypertrophic chondrocytes of the growth plate.

Circular Dichroism. Circular Dichroism spectra were recorded on a Jasco model 710 spectropolarimeter; peptides were analyzed at a concentrtion of 20 μM in 50 mM sodium phosphate buffer pH 7.4, or the same buffer containing 2,2, 2-trifluoroethanol at 20% (v/v). Spectroscopic scans were performed at 20° C. and at wavelengths between 185 and 255 nM, with data recored at each 1 nM interval. The spectral bandwidth was 1.5 nM and 8 scans were accumulated and averaged for each sample. At each wavelength, the mean residue elipticity [θ×100/l×C×n); where θ is the raw elipticity value (in dimensions of millidegree), 1 is the sample path length, C=is the molar peptide concentration, and n is the number of residues in the peptide (Bowen, W. P., and Jerman, J. C., *Trends in Pharmacol. Sci.* 16: 413-417 (1995)). The helical content of each peptide was estimated by dividing [θ] observed at 222 nM for that peptide by −28,100, which is the reported [θ]$_{222}$obs for a model helical decapeptide (Bowen, W. P., and Jerman, J. C., *Trends in Pharmacol. Sci.* 16: 413-417 (1995)).

Data Calculation. Calculations were performed using Microsoft® Excel. Nonlinear regression analyses of binding and cAMP dose-response data were performed using the four-parameter equation: $y_p=Min+[(Max-Min)/(1+(IC_{50}/x)^{slope})]$. The Excel Solver function was utilized for parameter optimization, as described previously (Carter, P. H., et al., *Endocrinology* 140: 4972-4981 (1999); Bowen, W. P., and Jerman, J. C., *Trends in Pharmacol. Sci.* 16: 413-417 (1995)). Differences between paired data sets were statistically evaluated using a one-tailed Student's t-test, assuming unequal variances for the two sets.

Example 2

Substitutions in PTH(1-11) Analogs

The functional effects of substitutions at positions 6 and 10 in PTH using a PTH(1-11) analog AlaValAlaGluIleGlnLeuMetHisGlnArg-amide as the scaffold peptide (SEQ. ID. NO. 8). The peptides were analyzed for the capacity to stimulate cAMP formation in HKRK-B7 cells, an LLC-PK$_1$-derived cell line that expresses via stable transfection the recombinant human P1R at high density (~950,000 receptors per cell). The parent peptide PTH(1-11) elicited a 75-fold increase in cAMP formation with a corresponding $EC_{50}$ of 5.0±0.5 μM. Substitution of Gln$^6$ with Ala resulted in a marked reduction in potency, as the $EC_{50}$ observed for [Ala$^6$]PTH(1-11)(SEQ. ID. NO. 18) (330±40 μM) was 65-fold higher than that observed for PTH(1-11)(SEQ. ID. NO. 8) (P=0.008) (Table 1). Replacement of Gln$^{10}$ with Ala resulted in a modest (two fold) reduction in potency ($EC_{50}$ of [Ala$^{10}$]PTh(1-11)(SEQ.

ID. NO. 19)=11±2 μM; P v. parent=0.035). Substitution of both Gln$^6$ and Gln$^{10}$ together with Ala did not result in a simple additive additive reduction in potency (a 130-fold reduction would have been so predicted), but instead, resulted in only a 31-fold reduction in potency. In other words, the potency of [Ala$^{6,10}$]PTH(1-11)(SEQ. ID. NO. 20) (EC$_{50}$=160±20 μM) was two-fold greater than that of [Ala$^6$] PTH(1-11)(SEQ. ID. NO.18)(P=0.02). Thus, the Gln$^{10}$->Ala substitution partially rescued the potency defect imposed by the Gln$^6$->Ala substitution, but it did not improve peptide potency when position 6 was occupied by Gln.

The two-domain hypothesis of the PTH-P1R interaction mechanism predicts that the effects of the substitutions at positions 6 and 10 observed with the above PTH(1-11) analogs involve interactions (direct or indirect) that occur within the juxtamembrane region of the receptor. To test this hypothesis, P1R-DelNt was utilized. P1R-DeNt is a P1R construct that is deleted for most of the N domain yet which retains nearly full capacity to be expressed on the cell surface and to stimulate cAMP formation in response to N-terminal PTH analogs, and an LLC-PK1-derived cell line was herein established, LdelNt-2, which stably expresses P1R-DelNt. In these cells, the parent peptide PTH(1-11)(SEQ. ID. NO. 8) elicited a 55-fold increase in cAMP formation and the corresponding EC$_{50}$ (320±40 μM) was 22-fold higher than that of the parent peptide. This reduction in potency was partially rescued by the Gln$^{10}$->Ala substitution, as the potency of the [Ala$^{6,10}$] PTH(1-11)(SEQ. ID. NO. 20)(EC$_{50}$=170±50 μM) was two-fold lower than that of [Ala$^6$]PTH(1-11)(SEQ. ID. NO.18) (P=0.05). As was observed with the wild-type P1R, the analog [Ala$^6$]PTH(1-11)(SEQ. ID. NO. 19) (Gln at position 6) was ~3-fold less potent than PTH (1-11), thus, the enhancing effect of the Ala-10 substitution was observed when position 6 was Ala, but not when this position was Gln. These data obtained with P1R-DelNt parallel those obtained with the wild-type P1R and indicate that the functional effects of the substitutions at positions 6 and 10 are mediated via the J domain of the receptor.

TABLE 1 cAMP Responses of PTH(1-11) Analogs to HKRK-B7 Cells

| Peptide | EC$_{50}$ (μm) | E$_{max}$ (%) |
|---|---|---|
| PTH(1-11)(SEQ. ID. NO. 8) | 5.0 ± 0.5 | 100 ± 3 |
| [Ala$^6$]PTH(1-11) (SEQ. ID. NO. 18) | 330 ± 40 | 26 ± 2 |
| [Ala$^{10}$]PTH(1-11) (SEQ. ID. NO. 19) | 11 ± 2 | 88 ± 5 |
| [Ala$^6$, Ala$^{10}$]PTH(1-11) (SEQ. ID. NO. 20) | 160 ± 20 | 41 ± 2 |

Example 3

6-10 Rescue Effects in PTH(1-14)

Further examined was whether or not the 6-10 rescue effects could be observed in a conformationally constrained PTH(1-14) scaffold analog, [Aib$^{1,3}$] PTH(1-14)(AibV-alAibEIQLMHQHarAKW-amide) (SEQ. ID. NO.9) which, as was recently shown, has a higher potency and higher helical content than does the corresponding PTH(1-14) peptide containing alanine at positions 1 and 3. In LdelNt-2 cells, [Aib]PTH(1-14)(SEQ. ID. NO. 9) elicited a 50-fold increase in cAMP accumulation and the corresponding EC$_{50}$ value was 6.6±1.1 nM. Substituting Gln$^6$ of this peptide with alanine strongly reduced potency, as [Aib$^{1,3}$, Ala$^6$,]PTH(1-14) (SEQ. ID. NO.21)(EC$_{50}$=150±60 nM) was 22-fold weaker than the present peptide (P=0.08). The potency of [Aib$^{1,3}$, Ala$^{10}$]PTH(1-14)(SEQ. ID. NO. 22)(EC$_{50}$=81±65 nM) was 12-fold weaker than that of the parent peptide (P=0.18), but combining the Ala$^{10}$ substitution with the Ala$^6$ substitution, again resulted in a partial rescue of the signaling defect imposed by the Ala$^6$ substitution, as the potency of [Aib$^{1,3}$, Ala$^{6,10}$]PTH(1-14)(SEQ. ID. NO. 23) (EC$_{50}$=24±7 nM) was six-fold higher than that of [Aib$^{1,3}$, Ala$^6$]PTH(1-14)(SEQ. ID. NO. 21)(P=0.09) (see Table 2 below).

TABLE 2 cAMP Responses of PTH Analogs in L. DelNt-2 Cells

| Peptide | EC$_{50}$ (μm) | E$_{max}$ (%) |
|---|---|---|
| PTH(1-11)(SEQ. ID. NO. 8) | 14 ± 3 | 100 ± 2 |
| [Ala$^6$]PTH(1-11)(SEQ. ID. NO. 18) | 320 ± 40 | 14 ± 2 |
| [Ala$^{10}$]PTH(1-11)(SEQ. ID. NO. 19) | 39 ± 11 | 79 ± 5 |
| [Ala$^6$, Ala$^{10}$]PTH(1-11) (SEQ. ID. NO. 20) | 170 ± 50 | 42 ± 5 |
| | nM | |
| [Aib]PTH(1-14) (SEQ. ID. NO. 9) | 6.6 ± 1.1 | 100 ± 2 |
| [Aib$^{1,3}$, Ala$^6$]PTH(1-14) (SEQ. ID. NO. 21) | 146 ± 63 | 101 ± 4 |
| [Aib$^{1,3}$, Ala$^{10}$]PTH(1-14) (SEQ. ID. NO. 22) | 81 ± 65 | 104 ± 7 |
| [Aib$^{1,3}$, Ala$^{6,10}$]PTH(1-14) (SEQ. ID. NO. 23) | 24 ± 7 | 100 ± 3 |

Example 4

PTH(1-14) Analogs with 6-10 Lactam Bridges

The effects of installing a direct covalent linkage between the side chains of the residues at positions 6 and 10 on PTH analog function were also assessed. To do this, paired Glu$^6$/ Lys$^{10}$ or Lys$^6$/Glu$^{10}$ substitutions were introduced into an otherwise non-constrained PTH(1-14) analog scaffold Ala-ValAlaGluIleGln LeuMetHisGlnHarAlaLysTrp-amide (SEQ. ID. NO. 11) and formed an amide bond between the carboxylate side chain group of the introduced glutamate residue and the amino side chain group of the introduced lysine residue. For controls, a portion of each Glu/Lys- or Lys/Glu-substituted PTH(1-14) analog was preserved in the non-bridged form. The four peptides: [Glu$^6$, Lys$^{10}$]PTH(1-14)(linear)(SEQ. ID. NO. 24), [(Glu$^6$,Lys$^{10}$)lac.]PTH(1-14) cyclized via a 6-10 lactam bridge)(SEQ. ID. NO. 3), [Lys$^6$, Glu$^{10}$]PTH(1-14)(SEQ. ID. NO. 25), and [(Lys$^6$, Glu$^{10}$)lac.] PTH(1-14)(SEQ. ID. NO. 26) were first compared at a single dose of 10 μM for the capacity to stimulate cAMP formulation in HKRK-B28 cells, an LLC-PK$_1$-derived cell line that expresses the recombinant full-length P1R at a moderate level (~280,000 receptors per cell). None of the four analogs was as effective as the parent PTH(1-14) analog in introducing a cAMP response. For the peptides containing the Glu$^6$/Lys$^{10}$ pairing, the activity of the lactam-containing analog was comparable to that of its linear counterpart. For the reciprocal analog containing the Lys$^6$/Glu$^{10}$ pairing, the bridged peptide was more active than its linear counterpart. In dose-response analyses, [Lys$^6$,Glu$^{10}$)lac.]PTH(1-14) (SEQ. ID. NO. 3) was six-fold more potent than [Lys$^6$, Glu$^{10}$]PTH(1-14)(P=0.02) (SEQ. ID. NO. 25). (See Table 3 below).

TABLE 3

Effect of a 6-10 Lactam Bridge on PTH(1-14) Potency in HKRK-828 Cells

| Peptide | EC$_{50}$ (μm) | E$_{max}$ (%) |
|---|---|---|
| PTH(1-14) (SEQ. ID. NO. 11) | 0.12 ± 0.04 | 100 ± 2 |
| [Glu$^6$, Lys$^{10}$]PTH(1-14) (SEQ. ID. NO. 24) | 40 ± 6 | 52 ± 3 |
| [(Glu$^6$, Lys$^{10}$)lac.]PTH(1-14) (SEQ. ID. NO. 3) | 27 ± 9 | 52 ± 3 |
| [Lys$^6$, Glu$^{10}$]PTH(1-14) (SEQ. ID. NO. 25) | 130 ± 30 | 37 ± 5 |
| [(Lys$^6$, Glu$^{10}$)lac.]PTH(1-14) (SEQ. ID. NO. 26) | 21 ± 6 | 59 ± 3 |

Example 5

Substitutions in PTH(1-34) Analogs

The functional effects of substitutions at positions 6 and 10 in a PTH(1-34) scaffold peptide ([Tyr$^{34}$]hPTh(1-34)amide) (SEQ. ID. NO. 10) were investigated. The analogs were prepared with either Gln (native) or Ala at position 6 and either Asn (native) or Ala at position 10. The potencies of these peptides were compared, and the wild-type P1R expressed transiently in COS-7 cells as well as stable in HKRK-B28 cells. In either cell system, no difference in potency could be discerned for the four analogs, nor was any difference in apparent binding affinity of the analogs detected in HKRK-B28 cells. In COS-7 cells expressing P1R-DelNt, however, differences in cAMP-signaling potencies could be detected. Thus, the Gln$^{10}$->Ala substitution had no effect on the PTH (1-34) potency, the Gln$^6$->Ala substitution abolished signaling activity, and addition of the Gln$^{10}$->Ala substitution to the Gln$^6$->Ala substitution completely restored activity, as [Ala$^{6,10}$]PTH(1-34)(SEQ. ID. NO. 27) was as potent as PTH (1-34).

Table 4 shows cAMP responses of PTH(1-34) analogs in COS-7 cells. The peptide PTH(1-34)([Tyr$^{34}$]hPTH(1-34)NH$_2$)(SEQ. ID. NO. 11) and analogs containing the indicated residues at positions 6 and/or 10 were evaluated for the capacity to stimulate cAMP accumulation in COS-7 cells transiently transfected with either the wild-type P1R(P1R-WT) or P1R-DelNt. EC$_{50}$ values were calculated by non-linear regression analysis; the maximum response observed (E$_{MAX}$) for each peptide, at concentrations of 1×10$^{-6}$M for P1R-WT and 1×10$^{-5}$ for P1RDelNt, is given as a percent of the maximum response observed for PTH(1-34) acting on P1R-WT, the average of which was 294±15 pM per well. The corresponding basal cAMP values (not subtracted) for P1R-WT and P1R-delNt were 5.6±0.1 pM per well and 4.2±0.4 pM per well, respectively.

TABLE 4 cAMP Responses of PTH(1-34) Analogs in COS-7 Cells

| | P1R-WT | | P1R-DelNt | |
|---|---|---|---|---|
| Peptide | EC$_{50}$ (μm) | E$_{max}$ (%) | EC$_{50}$ (μm) | E$_{max}$ (%) |
| PTH(1-34) (SEQ. ID. NO. 10) | 0.27 ± 0.11 | 100 ± 1 | 15 ± 5 | 44 ± 2 |
| [Ala$^6$]PTH(1-34) (SEQ. ID. NO. 28) | 0.17 ± 0.01 | 104 ± 2 | >100 | 4.5 ± 0.9 |
| [Ala$^{10}$]PTH(1-34) (SEQ. ID. NO. 29) | 0.27 ± 0.07 | 96 ± 4 | 14 ± 4 | 46 ± 2 |
| [Ala$^{6,10}$]PTH(1-34) (SEQ. ID. NO. 27) | 0.30 ± 0.03 | 121 ± 7 | 19 ± 9 | 44 ± 2 |

Table 5 shows the functional properties of PTH(1-34) analogs in HKRK-B28 cells. The peptide PTH(1-34) ([Tyr$^{34}$]$_b$ PTH(1-34)NH$_2$) (SEQ. ID. NO. 10) and analogs containing substitutions at positions 6 and/or 10 in place of Gln and Asn, respectively, were evaluated in HKRK-B28 cells for the capacity to stimulate cAMP accumulation, and to inhibit the binding of $^{125}$I-[Ala$^{3,12}$, Gln$^{10}$, Har$^{11}$, Trp$^{14}$,Arg$^{19}$, Tyr$^{21}$] PTH(1-21)-amide (SEQ. ID. NO.30) tracer radioligand. IC$_{50}$ and EC$_{50}$ values were calcuated by non-linear regression analysis; the maximum cAMP response observed (E$_{MAX}$) for each peptide at a concentration of 1×10$^{-6}$ M is given as a percent of the maximum response observed for PTH(1-34), the average of which was 416±51 pM per well.

TABLE 5

Functional Properties of PTH(1-34) Analogs in HKRK-828 Cells

| | cAMP | | Binding |
|---|---|---|---|
| Peptide | EC$_{50}$ (μm) | E$_{max}$ (%) | IC$_{50}$ (μm) |
| PTH(1-34) (SEQ. ID. NO. 10) | 1.9 ± 0.8 | 100 ± 5 | 6.0 ± 3.2 |
| [Ala$^6$]PTH(1-34) (SEQ. ID. NO. 28) | 4.9 ± 3.6 | 105 ± 10 | 4.5 ± 1.4 |
| [Ala$^{10}$]PTH(1-34) (SEQ. ID. NO. 29) | 3.0 ± 1.3 | 106 ± 7 | 6.4 ± 2.8 |
| [Ala$^{6,10}$]PTH(1-34) (SEQ. ID. NO. 27) | 2.2 ± 0.3 | 107 ± 8 | 3.9 ± 1.1 |

Having now fully described the present invention in some detail by way of illustration and example for purposes of clarity of understanding, it will be obvious to one of ordinary skill in the art that the same can be performed by modifying or changing the invention with a wide and equivalent range of conditions, formulations and other parameters thereof, and that such modifications or changes are intended to be encompassed within the scope of the appended claims.

All publications, patents and patent applications mentioned herein above are herein incorporated in their entirety and by reference to the same extent as if each individual publication, patent or patent application was specifically and individually indicated to be incorporated by reference.

SEQUENCE LISTING

<160> NUMBER OF SEQ ID NOS: 37

<210> SEQ ID NO 1
<211> LENGTH: 14
<212> TYPE: PRT
<213> ORGANISM: Artificial Sequence
<220> FEATURE:
<223> OTHER INFORMATION: Mutated hPTH
<220> FEATURE:
<221> NAME/KEY: MISC_FEATURE
<222> LOCATION: (1)..(1)
<223> OTHER INFORMATION: Xaa can represent Gly, Ser, Ala or alpha-
      aminoisobutyric acid
<220> FEATURE:
<221> NAME/KEY: MISC_FEATURE
<222> LOCATION: (3)..(3)
<223> OTHER INFORMATION: Xaa can represent Ala, Ser, alpha-
      aminoisobutyric acid
<220> FEATURE:
<221> NAME/KEY: MISC_FEATURE
<222> LOCATION: (6)..(6)
<223> OTHER INFORMATION: Xaa can represent Asp, Glu or Lys
<220> FEATURE:
<221> NAME/KEY: MISC_FEATURE
<222> LOCATION: (10)..(10)
<223> OTHER INFORMATION: Xaa can represent Asp, Glu or Lys
<220> FEATURE:
<221> NAME/KEY: MISC_FEATURE
<222> LOCATION: (11)..(11)
<223> OTHER INFORMATION: Xaa can represent Arg, Leu or Homoarginine
<220> FEATURE:
<221> NAME/KEY: MISC_FEATURE
<222> LOCATION: (12)..(12)
<223> OTHER INFORMATION: Xaa can represent Ala or Gly
<220> FEATURE:
<221> NAME/KEY: MISC_FEATURE
<222> LOCATION: (14)..(14)
<223> OTHER INFORMATION: Xaa can represent Trp or His
<220> FEATURE:
<221> NAME/KEY: MOD_RES
<222> LOCATION: (14)..(14)
<223> OTHER INFORMATION: AMIDATION

<400> SEQUENCE: 1

Xaa Val Xaa Glu Ile Xaa Leu Met His Xaa Xaa Xaa Lys Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Mutated hPTH
<220> FEATURE:
<221> NAME/KEY: MISC_FEATURE
<222> LOCATION: (6)..(6)
<223> OTHER INFORMATION: Xaa can represent Asp, Glu or Lys
<220> FEATURE:
<221> NAME/KEY: MISC_FEATURE
<222> LOCATION: (9)..(9)
<223> OTHER INFORMATION: Xaa represents homoarginine
<220> FEATURE:
<221> NAME/KEY: MOD_RES
<222> LOCATION: (12)..(12)
<223> OTHER INFORMATION: AMIDATION

<400> SEQUENCE: 2

Ala Val Ala Glu Ile Xaa Leu Met Xaa Ala Lys Trp
1               5                   10

<210> SEQ ID NO 3
<211> LENGTH: 14

```
<212> TYPE: PRT
<213> ORGANISM: Artificial Sequence
<220> FEATURE:
<223> OTHER INFORMATION: [(Glu-6, Lys-10)lac.]PTH(1-14)
<220> FEATURE:
<221> NAME/KEY: MISC_FEATURE
<222> LOCATION: (1)..(14)
<223> OTHER INFORMATION: Sequence is cyclized via a 6-10 lactam bridge
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 3

Ala Val Ala Glu Ile Glu Leu Met His Lys Xaa Ala Lys Trp
1               5                   10

<210> SEQ ID NO 4
<211> LENGTH: 14
<212> TYPE: PRT
<213> ORGANISM: Artificial Sequence
<220> FEATURE:
<223> OTHER INFORMATION: [(Lys-6, Lys-10)lac.]PTH(1-14)
<220> FEATURE:
<221> NAME/KEY: MISC_FEATURE
<222> LOCATION: (1)..(14)
<223> OTHER INFORMATION: Sequence is cyclized via 6-10 lactam bridge
<220> FEATURE:
<221> NAME/KEY: MOD_RES
<222> LOCATION: (14)..(14)
<223> OTHER INFORMATION: AMIDATION

<400> SEQUENCE: 4

Ala Val Ala Glu Ile Lys Leu Met His Lys Xaa Ala Lys Trp
1               5                   10

<210> SEQ ID NO 5
<211> LENGTH: 34
<212> TYPE: PRT
<213> ORGANISM: Rattus sp.
<220> FEATURE:
<221> NAME/KEY: MOD_RES
<222> LOCATION: (34)..(34)
<223> OTHER INFORMATION: AMIDATION

<400> SEQUENCE: 5

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe

<210> SEQ ID NO 6
<211> LENGTH: 34
<212> TYPE: PRT
<213> ORGANISM: Homo sapiens
<220> FEATURE:
<221> NAME/KEY: MOD_RES
<222> LOCATION: (34)..(34)
<223> OTHER INFORMATION: AMIDATION

<400> SEQUENCE: 6

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
```

```
                          20                  25                  30
Asn Phe

<210> SEQ ID NO 7
<211> LENGTH: 34
<212> TYPE: PRT
<213> ORGANISM: Artificial Sequence
<220> FEATURE:
<223> OTHER INFORMATION: Mutated hPTH
<220> FEATURE:
<221> NAME/KEY: MISC_FEATURE
<222> LOCATION: (6)..(6)
<223> OTHER INFORMATION: Xaa can represent Ala, Glu or Gln
<220> FEATURE:
<221> NAME/KEY: MISC_FEATURE
<222> LOCATION: (10)..(10)
<223> OTHER INFORMATION: Xaa can represent Ala, Glu or Gln
<220> FEATURE:
<221> NAME/KEY: MOD_RES
<222> LOCATION: (34)..(34)
<223> OTHER INFORMATION: AMIDATION

<400> SEQUENCE: 7

Ser Val Ser Glu Ile Xaa Leu Met His Xaa Leu Gly Lys His Leu Asn
1               5                   10                  15

Ser Met Glu Arg Val Glu Trp Leu Arg Lys Lys Leu Gln Asp Val His
            20                  25                  30

Asn Tyr

<210> SEQ ID NO 8
<211> LENGTH: 11
<212> TYPE: PRT
<213> ORGANISM: Artificial Sequence
<220> FEATURE:
<223> OTHER INFORMATION: Mutated hPTH(1-11)
<220> FEATURE:
<221> NAME/KEY: MOD_RES
<222> LOCATION: (11)..(11)
<223> OTHER INFORMATION: AMIDATION

<400> SEQUENCE: 8

Ala Val Ala Glu Ile Gln Leu Met His Gln Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: [Aib-1,3]PTH(1-14)
<220> FEATURE:
<221> NAME/KEY: MISC_FEATURE
<222> LOCATION: (1)..(1)
<223> OTHER INFORMATION: Xaa represents alpha-aminoisobutyric acid
<220> FEATURE:
<221> NAME/KEY: MISC_FEATURE
<222> LOCATION: (3)..(3)
<223> OTHER INFORMATION: Xaa represents alpha-aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 9

Xaa Val Xaa Glu Ile Gln Leu Met His Gln Xaa Ala Lys Trp
1               5                   10
```

```
<210> SEQ ID NO 10
<211> LENGTH: 34
<212> TYPE: PRT
<213> ORGANISM: Artificial Sequence
<220> FEATURE:
<223> OTHER INFORMATION: ([Tyr-34]hPTH(1-34)amide)
<220> FEATURE:
<221> NAME/KEY: MOD_RES
<222> LOCATION: (34)..(34)
<223> OTHER INFORMATION: AMIDATION

<400> SEQUENCE: 10

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Tyr

<210> SEQ ID NO 11
<211> LENGTH: 14
<212> TYPE: PRT
<213> ORGANISM: Artificial Sequence
<220> FEATURE:
<223> OTHER INFORMATION: [Ala-1,3,12, Gln-10, Har-11, Trp-14]PTH(1-14)
      amide
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 11

Ala Val Ala Glu Ile Gln Leu Met His Gln Xaa Ala Lys Trp
1               5                   10

<210> SEQ ID NO 12
<211> LENGTH: 11
<212> TYPE: PRT
<213> ORGANISM: Artificial Sequence
<220> FEATURE:
<223> OTHER INFORMATION: [Ala-1,3, Gln-10, Har-11]PTH(1-11)amide
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (11)..(11)
<223> OTHER INFORMATION: AMIDATION

<400> SEQUENCE: 12

Ala Val Ala Glu Ile Gln Leu Met His Gln Xaa
1               5                   10

<210> SEQ ID NO 13
<211> LENGTH: 84
<212> TYPE: PRT
<213> ORGANISM: Homo sapiens
<220> FEATURE:
<221> NAME/KEY: MOD_RES
<222> LOCATION: (84)..(84)
<223> OTHER INFORMATION: AMIDATION

<400> SEQUENCE: 13

Ser Val Ser Glu Ile Gln Leu Met His Asn Leu Gly Lys His Leu Asn
```

```
                1               5                  10                  15
Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
                35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 14
<211> LENGTH: 21
<212> TYPE: PRT
<213> ORGANISM: Artificial Sequence
<220> FEATURE:
<223> OTHER INFORMATION: [M]PTH(1-21)
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (21)..(21)
<223> OTHER INFORMATION: AMIDATION

<400> SEQUENCE: 14

Ala Val Ala Glu Ile Gln Leu Met His Gln Xaa Ala Lys Trp Leu Asn
1               5                   10                  15

Ser Met Glu Arg Val
                20

<210> SEQ ID NO 15
<211> LENGTH: 21
<212> TYPE: PRT
<213> ORGANISM: Artificial Sequence
<220> FEATURE:
<223> OTHER INFORMATION: [Aib-1,3, M]PTH(1-21)
<220> FEATURE:
<221> NAME/KEY: MISC_FEATURE
<222> LOCATION: (1)..(1)
<223> OTHER INFORMATION: Xaa represents alpha-aminoisobutyric acid
<220> FEATURE:
<221> NAME/KEY: MISC_FEATURE
<222> LOCATION: (3)..(3)
<223> OTHER INFORMATION: Xaa represents alpha-aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (21)..(21)
<223> OTHER INFORMATION: AMIDATION

<400> SEQUENCE: 15

Xaa Val Xaa Glu Ile Gln Leu Met His Gln Xaa Ala Lys Trp Leu Asn
1               5                   10                  15

Ser Met Glu Arg Val
                20

<210> SEQ ID NO 16
<211> LENGTH: 21
<212> TYPE: PRT
<213> ORGANISM: Artificial Sequence
<220> FEATURE:
<223> OTHER INFORMATION: [M]PTH(1-21) radiolabeled with Iodine isotope
```

```
            125
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (21)..(21)
<223> OTHER INFORMATION: AMIDATION

<400> SEQUENCE: 16

Ala Val Ala Glu Ile Gln Leu Met His Gln Xaa Ala Lys Trp Leu Asn
1               5                   10                  15

Ser Met Glu Arg Val
            20

<210> SEQ ID NO 17
<211> LENGTH: 21
<212> TYPE: PRT
<213> ORGANISM: Artificial Sequence
<220> FEATURE:
<223> OTHER INFORMATION: [Aib-1,3, M]PTH(1-21) radiolabeled with Iodine
      isotope 125
<220> FEATURE:
<221> NAME/KEY: MISC_FEATURE
<222> LOCATION: (1)..(1)
<223> OTHER INFORMATION: Xaa represents alpha-aminoisobutyric acid
<220> FEATURE:
<221> NAME/KEY: MISC_FEATURE
<222> LOCATION: (3)..(3)
<223> OTHER INFORMATION: Xaa represents alpha-aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (21)..(21)
<223> OTHER INFORMATION: AMIDATION

<400> SEQUENCE: 17

Xaa Val Xaa Glu Ile Gln Leu Met His Gln Xaa Ala Lys Trp Leu Asn
1               5                   10                  15

Ser Met Glu Arg Val
            20

<210> SEQ ID NO 18
<211> LENGTH: 11
<212> TYPE: PRT
<213> ORGANISM: Artificial Sequence
<220> FEATURE:
<223> OTHER INFORMATION: [Ala-6]PTH(1-11)
<220> FEATURE:
<221> NAME/KEY: MOD_RES
<222> LOCATION: (11)..(11)
<223> OTHER INFORMATION: AMIDATION

<400> SEQUENCE: 18

Ala Val Ala Glu Ile Ala Leu Met His Gln Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: [Ala-10]PTH(1-11)
<220> FEATURE:
<221> NAME/KEY: MOD_RES
<222> LOCATION: (11)..(11)
<223> OTHER INFORMATION: AMIDATION
```

<400> SEQUENCE: 19

Ala Val Ala Glu Ile Gln Leu Met His Ala Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: [Ala-6,10]PTH(1-11)
<220> FEATURE:
<221> NAME/KEY: MOD_RES
<222> LOCATION: (11)..(11)
<223> OTHER INFORMATION: AMIDATION

<400> SEQUENCE: 20

Ala Val Ala Glu Ile Ala Leu Met His Ala Arg
1               5                   10

<210> SEQ ID NO 21
<211> LENGTH: 14
<212> TYPE: PRT
<213> ORGANISM: Artificial Sequence
<220> FEATURE:
<223> OTHER INFORMATION: [Ala-6, Aib-1,3]PTH(1-14)
<220> FEATURE:
<221> NAME/KEY: MISC_FEATURE
<222> LOCATION: (1)..(1)
<223> OTHER INFORMATION: Xaa represents alpha-aminoisobutyric acid
<220> FEATURE:
<221> NAME/KEY: MISC_FEATURE
<222> LOCATION: (3)..(3)
<223> OTHER INFORMATION: Xaa represents alpha-aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 21

Xaa Val Xaa Glu Ile Ala Leu Met His Gln Xaa Ala Lys Trp
1               5                   10

<210> SEQ ID NO 22
<211> LENGTH: 14
<212> TYPE: PRT
<213> ORGANISM: Artificial Sequence
<220> FEATURE:
<223> OTHER INFORMATION: [Aib-1,3, Ala-10]PTH(1-14)
<220> FEATURE:
<221> NAME/KEY: MISC_FEATURE
<222> LOCATION: (1)..(1)
<223> OTHER INFORMATION: Xaa represents alpha-aminoisobutyric acid
<220> FEATURE:
<221> NAME/KEY: MISC_FEATURE
<222> LOCATION: (3)..(3)
<223> OTHER INFORMATION: Xaa represents alpha-aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 22

Xaa Val Xaa Glu Ile Gln Leu Met His Ala Xaa Ala Lys Trp

-continued

```
<210> SEQ ID NO 23
<211> LENGTH: 14
<212> TYPE: PRT
<213> ORGANISM: Artificial Sequence
<220> FEATURE:
<223> OTHER INFORMATION: [Aib-1,3, Ala-6,10]PTH(1-14)
<220> FEATURE:
<221> NAME/KEY: MISC_FEATURE
<222> LOCATION: (1)..(1)
<223> OTHER INFORMATION: Xaa represents alpha-aminoisobutyric acid
<220> FEATURE:
<221> NAME/KEY: MISC_FEATURE
<222> LOCATION: (3)..(3)
<223> OTHER INFORMATION: Xaa represents alpha-aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 23

Xaa Val Xaa Glu Ile Ala Leu Met His Ala Xaa Ala Lys Trp
1               5                   10

<210> SEQ ID NO 24
<211> LENGTH: 14
<212> TYPE: PRT
<213> ORGANISM: Artificial Sequence
<220> FEATURE:
<223> OTHER INFORMATION: [Glu-6, Lys-10]PTH(1-14)(linear)
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 24

Ala Val Ala Glu Ile Glu Leu Met His Lys Xaa Ala Lys Trp
1               5                   10

<210> SEQ ID NO 25
<211> LENGTH: 14
<212> TYPE: PRT
<213> ORGANISM: Artificial Sequence
<220> FEATURE:
<223> OTHER INFORMATION: [Lys-6, Glu-10]PTH(1-14)(linear)
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 25

Ala Val Ala Glu Ile Lys Leu Met His Glu Xaa Ala Lys Trp
1               5                   10

<210> SEQ ID NO 26
<211> LENGTH: 14
<212> TYPE: PRT
<213> ORGANISM: Artificial Sequence
<220> FEATURE:
```

```
<223> OTHER INFORMATION: [(Lys-6, Glu-10)lac.]PTH(1-14)
<220> FEATURE:
<221> NAME/KEY: MISC_FEATURE
<222> LOCATION: (1)..(14)
<223> OTHER INFORMATION: Sequence is cyclized via a 6-10 lactam bridge
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 26

Ala Val Ala Glu Ile Lys Leu Met His Glu Xaa Ala Lys Trp
1               5                   10

<210> SEQ ID NO 27
<211> LENGTH: 34
<212> TYPE: PRT
<213> ORGANISM: Artificial Sequence
<220> FEATURE:
<223> OTHER INFORMATION: [Ala-6,10]PTH(1-34)
<220> FEATURE:
<221> NAME/KEY: MOD_RES
<222> LOCATION: (34)..(34)
<223> OTHER INFORMATION: AMIDATION

<400> SEQUENCE: 27

Ser Val Ser Glu Ile Ala Leu Met His Ala Leu Gly Lys His Leu Asn
1               5                   10                  15

Ser Met Glu Arg Val Glu Trp Leu Arg Lys Lys Leu Gln Asp Val His
            20                  25                  30

Asn Tyr

<210> SEQ ID NO 28
<211> LENGTH: 34
<212> TYPE: PRT
<213> ORGANISM: Artificial Sequence
<220> FEATURE:
<223> OTHER INFORMATION: [Ala-6,10]PTH(1-34)
<220> FEATURE:
<221> NAME/KEY: MOD_RES
<222> LOCATION: (34)..(34)
<223> OTHER INFORMATION: AMIDATION

<400> SEQUENCE: 28

Ser Val Ser Glu Ile Ala Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Tyr

<210> SEQ ID NO 29
<211> LENGTH: 34
<212> TYPE: PRT
<213> ORGANISM: Artificial Sequence
<220> FEATURE:
<223> OTHER INFORMATION: [Ala-10]PTH(1-34)
<220> FEATURE:
<221> NAME/KEY: MOD_RES
<222> LOCATION: (34)..(34)
<223> OTHER INFORMATION: AMIDATION

<400> SEQUENCE: 29

Ser Val Ser Glu Ile Gln Leu Met His Ala Leu Gly Lys His Leu Asn
1               5                   10                  15
```

```
Ser Met Glu Arg Val Glu Trp Leu Arg Lys Lys Leu Gln Asp Val His
            20                  25                  30

Asn Tyr

<210> SEQ ID NO 30
<211> LENGTH: 21
<212> TYPE: PRT
<213> ORGANISM: Artificial Sequence
<220> FEATURE:
<223> OTHER INFORMATION: [Ala-3,12, Gln-10, Har-11, Trp-14, Arg-19,
      Tyr-21]PTH(1-21)amide radiolabeled with Iodine isotope 125
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (21)..(21)
<223> OTHER INFORMATION: AMIDATION

<400> SEQUENCE: 30

Ser Val Ala Glu Ile Gln Leu Met His Gln Xaa Ala Lys Trp Leu Asn
1               5                   10                  15

Ser Met Arg Arg Tyr
            20

<210> SEQ ID NO 31
<211> LENGTH: 34
<212> TYPE: PRT
<213> ORGANISM: Artificial Sequence
<220> FEATURE:
<223> OTHER INFORMATION: Mutated hPTH(1-34)
<220> FEATURE:
<221> NAME/KEY: MISC_FEATURE
<222> LOCATION: (1)..(1)
<223> OTHER INFORMATION: Xaa can represent Gly, Ser, Ala or alpha-
      aminoisobutyric acid
<220> FEATURE:
<221> NAME/KEY: MISC_FEATURE
<222> LOCATION: (3)..(3)
<223> OTHER INFORMATION: Xaa can represent Ser, Ala or alpha-
      aminoisobutyric acid
<220> FEATURE:
<221> NAME/KEY: MISC_FEATURE
<222> LOCATION: (6)..(6)
<223> OTHER INFORMATION: Xaa can represent Asp, Glu or Lys
<220> FEATURE:
<221> NAME/KEY: MISC_FEATURE
<222> LOCATION: (10)..(10)
<223> OTHER INFORMATION: Xaa can represent Asp, Glu or Lys
<220> FEATURE:
<221> NAME/KEY: MISC_FEATURE
<222> LOCATION: (11)..(11)
<223> OTHER INFORMATION: Xaa can represent Arg, Har or Leu
<220> FEATURE:
<221> NAME/KEY: MISC_FEATURE
<222> LOCATION: (12)..(12)
<223> OTHER INFORMATION: Xaa can represent Ala or Gly
<220> FEATURE:
<221> NAME/KEY: MISC_FEATURE
<222> LOCATION: (14)..(14)
<223> OTHER INFORMATION: Xaa can represent Trp or His
<220> FEATURE:
<221> NAME/KEY: MOD_RES
<222> LOCATION: (14)..(14)
<223> OTHER INFORMATION: AMIDATION

<400> SEQUENCE: 31

Xaa Val Xaa Glu Ile Xaa Leu Met His Xaa Xaa Xaa Lys Xaa Leu Asn
1               5                   10                  15

Ser Met Glu Arg Val Glu Trp Leu Arg Lys Lys Leu Gln Asp Val His
```

-continued

```
                    20                  25                  30

Asn Tyr

<210> SEQ ID NO 32
<211> LENGTH: 21
<212> TYPE: PRT
<213> ORGANISM: Artificial Sequence
<220> FEATURE:
<223> OTHER INFORMATION: Mutated hPTH(1-21)
<220> FEATURE:
<221> NAME/KEY: MISC_FEATURE
<222> LOCATION: (1)..(1)
<223> OTHER INFORMATION: Xaa can represent Gly, Ser, Ala or alpha-
      aminoisobutyric acid
<220> FEATURE:
<221> NAME/KEY: MISC_FEATURE
<222> LOCATION: (3)..(3)
<223> OTHER INFORMATION: Xaa can represent Ser, Ala or alpha-
      aminoisobutyric acid
<220> FEATURE:
<221> NAME/KEY: MISC_FEATURE
<222> LOCATION: (6)..(6)
<223> OTHER INFORMATION: Xaa can represent Asp, Glu or Lys
<220> FEATURE:
<221> NAME/KEY: MISC_FEATURE
<222> LOCATION: (10)..(10)
<223> OTHER INFORMATION: Xaa can represent Asp, Glu or Lys
<220> FEATURE:
<221> NAME/KEY: MISC_FEATURE
<222> LOCATION: (11)..(11)
<223> OTHER INFORMATION: Xaa can represent Arg, Har or Leu
<220> FEATURE:
<221> NAME/KEY: MISC_FEATURE
<222> LOCATION: (12)..(12)
<223> OTHER INFORMATION: Xaa can represent Ala or Gly
<220> FEATURE:
<221> NAME/KEY: MISC_FEATURE
<222> LOCATION: (14)..(14)
<223> OTHER INFORMATION: Xaa can represent Trp or His
<220> FEATURE:
<221> NAME/KEY: MOD_RES
<222> LOCATION: (14)..(14)
<223> OTHER INFORMATION: AMIDATION

<400> SEQUENCE: 32

Xaa Val Xaa Glu Ile Xaa Leu Met His Xaa Xaa Xaa Lys Xaa Leu Asn
1               5                   10                  15

Ser Met Glu Arg Val
            20

<210> SEQ ID NO 33
<211> LENGTH: 13
<212> TYPE: PRT
<213> ORGANISM: Artificial Sequence
<220> FEATURE:
<223> OTHER INFORMATION: Mutated hPTH(1-13)
<220> FEATURE:
<221> NAME/KEY: MISC_FEATURE
<222> LOCATION: (1)..(1)
<223> OTHER INFORMATION: Xaa can represent Gly, Ser, Ala or alpha-
      aminoisobutyric acid
<220> FEATURE:
<221> NAME/KEY: MISC_FEATURE
<222> LOCATION: (3)..(3)
<223> OTHER INFORMATION: Xaa can represent Ser, Ala or alpha-
      aminoisobutyric acid
<220> FEATURE:
<221> NAME/KEY: MISC_FEATURE
<222> LOCATION: (6)..(6)
<223> OTHER INFORMATION: Xaa can represent Asp, Glu or Lys
<220> FEATURE:
<221> NAME/KEY: MISC_FEATURE
<222> LOCATION: (10)..(10)
<223> OTHER INFORMATION: Xaa can represent Asp, Glu or Lys
```

```
<220> FEATURE:
<221> NAME/KEY: MISC_FEATURE
<222> LOCATION: (11)..(11)
<223> OTHER INFORMATION: Xaa can represent Arg, Har or Leu
<220> FEATURE:
<221> NAME/KEY: MISC_FEATURE
<222> LOCATION: (12)..(12)
<223> OTHER INFORMATION: Xaa can represent Ala or Gly
<220> FEATURE:
<221> NAME/KEY: MOD_RES
<222> LOCATION: (13)..(13)
<223> OTHER INFORMATION: AMIDATION

<400> SEQUENCE: 33

Xaa Val Xaa Glu Ile Xaa Leu Met His Xaa Xaa Xaa Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Mutated hPTH(1-12)
<220> FEATURE:
<221> NAME/KEY: MISC_FEATURE
<222> LOCATION: (1)..(1)
<223> OTHER INFORMATION: Xaa can represent Gly, Ser, Ala or alpha-
      aminoisobutyric acid
<220> FEATURE:
<221> NAME/KEY: MISC_FEATURE
<222> LOCATION: (3)..(3)
<223> OTHER INFORMATION: Xaa can represent Ser, Ala or alpha-
      aminoisobutyric acid
<220> FEATURE:
<221> NAME/KEY: MISC_FEATURE
<222> LOCATION: (6)..(6)
<223> OTHER INFORMATION: Xaa can represent Asp, Glu or Lys
<220> FEATURE:
<221> NAME/KEY: MISC_FEATURE
<222> LOCATION: (10)..(10)
<223> OTHER INFORMATION: Xaa can represent Asp, Glu or Lys
<220> FEATURE:
<221> NAME/KEY: MISC_FEATURE
<222> LOCATION: (11)..(11)
<223> OTHER INFORMATION: Xaa can represent Arg, Har or Leu
<220> FEATURE:
<221> NAME/KEY: MISC_FEATURE
<222> LOCATION: (12)..(12)
<223> OTHER INFORMATION: Xaa can represent Ala or Gly
<220> FEATURE:
<221> NAME/KEY: MOD_RES
<222> LOCATION: (12)..(12)
<223> OTHER INFORMATION: AMIDATION

<400> SEQUENCE: 34

Xaa Val Xaa Glu Ile Xaa Leu Met His Xaa Xaa Xaa
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Mutated hPTH(1-11)
<220> FEATURE:
<221> NAME/KEY: MISC_FEATURE
<222> LOCATION: (1)..(1)
<223> OTHER INFORMATION: Xaa can represent Gly, Ser, Ala or alpha-
      aminoisobutyric acid
<220> FEATURE:
<221> NAME/KEY: MISC_FEATURE
<222> LOCATION: (3)..(3)
<223> OTHER INFORMATION: Xaa can represent Ser, Ala or alpha-
      aminoisobutyric acid
<220> FEATURE:
```

```
<221> NAME/KEY: MISC_FEATURE
<222> LOCATION: (6)..(6)
<223> OTHER INFORMATION: Xaa can represent Asp, Glu or Lys
<220> FEATURE:
<221> NAME/KEY: MISC_FEATURE
<222> LOCATION: (10)..(10)
<223> OTHER INFORMATION: Xaa can represent Asp, Glu or Lys
<220> FEATURE:
<221> NAME/KEY: MISC_FEATURE
<222> LOCATION: (11)..(11)
<223> OTHER INFORMATION: Xaa can represent Arg, Har or Leu
<220> FEATURE:
<221> NAME/KEY: MOD_RES
<222> LOCATION: (11)..(11)
<223> OTHER INFORMATION: AMIDATION

<400> SEQUENCE: 35

Xaa Val Xaa Glu Ile Xaa Leu Met His Xaa Xaa
1               5                   10

<210> SEQ ID NO 36
<211> LENGTH: 14
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: AMIDATION

<400> SEQUENCE: 36

Ser Val Ser Glu Ile Gln Leu Met His Asn Leu Gly Lys His
1               5                   10

<210> SEQ ID NO 37
<211> LENGTH: 14
<212> TYPE: PRT
<213> ORGANISM: Rattus sp.
<220> FEATURE:
<221> NAME/KEY: MOD_RES
<222> LOCATION: (14)..(14)
<223> OTHER INFORMATION: AMIDATION

<400> SEQUENCE: 37

Ala Val Ser Glu Ile Gln Leu Met His Asn Leu Gly Lys His
1               5                   10
```

What is claimed is:

1. A method for treating mammalian conditions characterized by decreases in bone mass, said method comprising administering to a subject in need thereof an effective bone mass-increasing amount of a biologically active peptide consisting essentially of the formula selected from:

(a)
$X_{01}$ValX$_{02}$GluIleX$_{03}$LeuMetHisX$_{04}$X$_{05}$X$_{06}$LysX$_{07}$Leu AsnSerMetGlu ArgValGluTrpLeuArgLysLysLeuGlnAspValHisAsnTyr-NH$_2$ (SEQ ID NO:31);

(b) a fragment of SEQ ID NO:31 containing the subsequence:
$X_{01}$ValX$_{02}$GluIleX$_{03}$LeuMetHisX$_{04}$X$_{05}$X$_{06}$LysX$_{07}$Leu;

(c) pharmaceutically acceptable salts thereof; or (d) N- or C-derivatives thereof; wherein $X_{01}$ is Gly, Ser, Ala or Aib;
$X_{02}$ is Ala, Ser or Aib;
$X_{03}$ is Asp, Glu or Lys;
$X_{04}$ is Asp, Glu or Lys;
$X_{05}$ is Arg, Har or Leu;
$X_{06}$ is Ala or Gly;
$X_{07}$ is Trp or His.

2. The method of claim 1, wherein said peptide is administered in conjunction with a pharmaceutically acceptable carrier.

3. The method of claim 1, wherein $X_{01}$ is Ser.

4. The method of claim 1, wherein $X_{02}$ is Ser.

5. The method of claim 1, wherein $X_{05}$ is Leu.

6. The method of claim 1, wherein $X_{06}$ is Gly.

7. The method of claim 1, wherein $X_{07}$ is His.

8. The method of claim 1, wherein $X_{01}$ is Ser, $X_{02}$ is Ser, $X_{05}$ is Leu, $X_{06}$ is Gly, and $X_{07}$ is His.

9. The method of claim 8, wherein $X_{03}$ is Glu and $X_{04}$ is Lys.

10. The method of claim 8, wherein said peptide is administered in conjunction with a pharmaceutically acceptable carrier.

11. The method of claim 1, wherein said condition is osteoporosis.

12. The method of claim 10, wherein said condition is old age osteoporosis.

13. The method of claim 10, wherein said condition is post-menopausal osteoporosis.

14. The method of claim 1, wherein said peptide is administered parenterally.

15. The method of claim 14, wherein said peptide is administered subcutaneously.

16. The method of claim 14, wherein said peptide is administered by nasal insufflation.

17. The method of claim 14, wherein said peptide is administered intravenously.

18. The method of claim 1, wherein said peptide is administered in an amount of about 0.01 µg/kg/day to about 1.0 µg/kg/day.

* * * * *

UNITED STATES PATENT AND TRADEMARK OFFICE
CERTIFICATE OF CORRECTION

| | |
|---|---|
| PATENT NO. | : 7,521,528 B2 |
| APPLICATION NO. | : 10/542704 |
| DATED | : April 21, 2009 |
| INVENTOR(S) | : Gardella et al. |

It is certified that error appears in the above-identified patent and that said Letters Patent is hereby corrected as shown below:

Column 1, Lines 33-34, replace "*Handbook of experimental Pharmacology*" with --*Handbook of Experimental Pharmacology*--.

Column 2, Line 54, replace "phospolipase C" with --phospholipase C-- .

Column 4, Line 19, replace "comprising to a subject" with --comprising administering to a subject--.

Column 6, Line 1, replace "flourescent" with --fluorescent--.

Column 12, Line 34, replace "P1TH" with --PTH--;

Lines 57-58, replace "PTH((1-84)" with --PTH(1-84)--;

Line 58, replace "PTH((1-34)" with --PTH(1-34)--.

Column 15, Line 26, replace "HKPK-B28" with --HKRK-B28--.

Column 16, Line 20, replace "concentrtion" with --concentration--;

Line 24, replace "recored" with --recorded--.

Column 17, Line 3, replace "additive additive" with --additive--.

Column 20, Line 28, replace "calcuated" with --calculated--.

Column 21, under SEQ ID NO 2, replace "<211> LENGTH: 12" with --<211> LENGTH: 14--;

Under SEQ ID NO 2, replace "<222> LOCATION: (9) .. (9)" with --<222> LOCATION: (11) .. (11)--;

Signed and Sealed this
Twentieth Day of March, 2012

David J. Kappos
*Director of the United States Patent and Trademark Office*

Under SEQ ID NO 2, replace "<222> LOCATION: (12) .. (12)" with
--<222> LOCATION: (14) .. (14)--;

Under SEQ ID NO 2, replace "Ala Val Ala Glu Ile Xaa Leu Met Xaa Ala Lys Trp" with
--Ala Val Ala Glu Ile Xaa Leu Met His Gln Xaa Ala Lys Trp--.

Column 23, under SEQ ID NO 3, replace "<223> OTHER INFORMATION:
[(Glu-6, Lys-10) lac.] PTH (l-14)" with --<223> OTHER INFORMATION: Mutated hPTH--;

Under SEQ ID NO 3, replace "<222> LOCATION: (1) .. (14)" with
--<222> LOCATION: (6) .. (10)--;

Under SEQ ID NO 3, replace "<223> OTHER INFORMATION: Sequence is cyclized via a 6-10 lactam bridge" with --<223> OTHER INFORMATION: Cyclization--;

Under SEQ ID NO 4, replace "<223> OTHER INFORMATION:
[(Lys-6, Lys-10) lac.] PTH (1-14)" with --<223> OTHER INFORMATION: Mutated hPTH--;

Column 23, under SEQ ID NO 4, replace "<222> LOCATION: (1) .. (14)" with
--<222> LOCATION: (6) .. (10)--;

Under SEQ ID NO 4, replace "<223> OTHER INFORMATION: Sequence is cyclized via 6-10 lactam bridge" with --<223> OTHER INFORMATION: Cyclization via lactam bridge--;

Under SEQ ID NO 4, insert
--<220> FEATURE:
<221> NAME/KEY: MISC_FEATURE
<222> LOCATION: (11) .. (11)
<223> OTHER INFORMATION: Xaa represents Har--.

Column 25, under SEQ ID NO 7, replace "<223> OTHER INFORMATION: Xaa can represent Ala, Glu, or Gln" with --<223> OTHER INFORMATION: Xaa can represent Lys, Glu, or Asp--;

Under SEQ ID NO 7, replace "<223> OTHER INFORMATION: Xaa can represent Ala, Glu, or Gln" with --<223> OTHER INFORMATION: Xaa can represent Glu, Asp, or Lys--;

CERTIFICATE OF CORRECTION (continued)

U.S. Pat. No. 7,521,528 B2

Under SEQ ID NO 9, replace "<223> OTHER INFORMATION: [Aib-1,3] PTH (1-14)" with --<223> OTHER INFORMATION: Mutated hPTH--.

Column 27, under SEQ ID NO 10, replace "<223> OTHER INFORMATION: (Tyr-34] hPTH (1-34) amide)" with --<223> OTHER INFORMATION: Mutated hPTH--;

Column 27, under SEQ ID NO 11, replace "<223> OTHER INFORMATION: [Ala-1,3,12, Gln-10, Har-11, Trp-14] PTH (1-14)amide" with --<223> OTHER INFORMATION: Mutated hPTH--;

Under SEQ ID NO 12, replace "<223> OTHER INFORMATION: [Ala-1,3, Gln-10, Har-11] PTH (1-11) amide" with --<223> OTHER INFORMATION: Mutated hPTH--.

Column 29, under SEQ ID NO 14, replace "<223> OTHER INFORMATION: [M] PTH (1-21)" with --<223> OTHER INFORMATION: Mutated hPTH--;

Under SEQ ID NO 15, replace "<223> OTHER INFORMATION:[Aib-1,3, M] PTH (1-21)" with --<223> OTHER INFORMATION: Mutated hPTH--;

Under SEQ ID NO 16, replace "<223> OTHER INFORMATION: [M] PTH (1-21) radiolabled with Iodine isotope 125" with --<223> OTHER INFORMATION: Mutated hPTH--.

Column 31, under SEQ ID NO 17, replace "<223> OTHER INFORMATION: [Aib-1,3, M] PTH (1-21) radiolabeled with Iodine isotope 125" with --<223> OTHER INFORMATION: Mutated hPTH--;

Under SEQ ID NO 18, replace "<223> OTHER INFORMATION: [Ala-6] PTH (1-11)" with --<223> OTHER INFORMATION: Mutated hPTH--;

Column 31, under SEQ ID NO 19, replace "<223> OTHER INFORMATION: [Ala-10] PTH (1-11)" with --<223> OTHER INFORMATION: Mutated hPTH--.

Column 33, under SEQ ID NO 20, replace "<223> OTHER INFORMATION: [Ala-6,10] PTH (1-11)" with --<223> OTHER INFORMATION: Mutated hPTH--;

CERTIFICATE OF CORRECTION (continued)

Under SEQ ID NO 21, replace "<223> OTHER INFORMATION:
[Ala-6, Aib-1,3] PTH (1-14)" with --<223> OTHER INFORMATION: Mutated hPTH--;

Under SEQ ID NO 22, replace "<223> OTHER INFORMATION:
[Aib-1,3, Ala-10] PTH (1-14)" with --<223> OTHER INFORMATION: Mutated hPTH--.

Column 35, under SEQ ID NO 23, replace "<223> OTHER INFORMATION:
[Aib-1,3, Ala-6,10] PTH (1-14)" with --<223> OTHER INFORMATION: Mutated hPTH--;

Under SEQ ID NO 24, replace "<223> OTHER INFORMATION:
[Glu-6, Lys-10] PTH (1-14) (linear)" with --<223> OTHER INFORMATION: Mutated hPTH--;

Under SEQ ID NO 25, replace "<223> OTHER INFORMATION:
[Lys-6, Glu-10] PTH (1-14) (linear)" with --<223> OTHER INFORMATION: Mutated hPTH--.

Column 37, under SEQ ID NO 26, replace "<223> OTHER INFORMATION:
[(Lys-6, Glu-10) lac.] PTH(1-14)" with --<223> OTHER INFORMATION: Mutated hPTH--;

Under SEQ ID NO 26, replace "<222> LOCATION: (1) .. (14)" with
--<222> LOCATION: (6) .. (10)--;

Under SEQ ID NO 26, replace "<223> OTHER INFORMATION: Sequence is cyclized via a 6-10 lactam bridge" with --<223> OTHER INFORMATION: Cyclization via lactam bridge--;

Under SEQ ID NO 27, replace "<223> OTHER INFORMATION: [Ala-6,10] PTH (1-34)" with --<223> OTHER INFORMATION: Mutated hPTH--;

Under SEQ ID NO 28, replace "<223> OTHER INFORMATION:
[Ala-6,10] PTH (1-34)" with --<223> OTHER INFORMATION: Mutated hPTH--;

Under SEQ ID NO 29, replace "<223> OTHER INFORMATION:
[Ala-10] PTH (1-34)" with --<223> OTHER INFORMATION: Mutated hPTH--.

CERTIFICATE OF CORRECTION (continued)
U.S. Pat. No. 7,521,528 B2

Column 39, under SEQ ID NO 30, replace "<223> OTHER INFORMATION: [Ala-3,12, Gln-10, Har-11, Trp-14, Arg-19, Tyr-21] PTH (1-21) amide radiolabeled with Iodine isotope 125" with --<223> OTHER INFORMATION: Mutated hPTH--.

Column 46, Line 50, replace "camer." with --carrier.--;

Column 46, Line 63, replace "camer." with --carrier.--.